(12) United States Patent
Lee et al.

(10) Patent No.: US 10,150,720 B2
(45) Date of Patent: Dec. 11, 2018

(54) DEVICE FOR PREPARING N-BUTANOL

(71) Applicant: LG CHEM, LTD., Seoul (KR)

(72) Inventors: Sung Kyu Lee, Daejeon (KR); Joon Ho Shin, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 524 days.

(21) Appl. No.: 14/646,325

(22) PCT Filed: Jan. 16, 2014

(86) PCT No.: PCT/KR2014/000483
§ 371 (c)(1),
(2) Date: May 20, 2015

(87) PCT Pub. No.: WO2014/112810
PCT Pub. Date: Jul. 24, 2014

(65) Prior Publication Data
US 2015/0299075 A1 Oct. 22, 2015

(30) Foreign Application Priority Data

Jan. 16, 2013 (KR) .................. 10-2013-0004944
Jan. 16, 2014 (KR) .................. 10-2014-0005344

(51) Int. Cl.
*C07C 29/80* (2006.01)
*B01D 3/14* (2006.01)

(52) U.S. Cl.
CPC .............. *C07C 29/80* (2013.01); *B01D 3/141* (2013.01)

(58) Field of Classification Search
None
See application file for complete search history.

(56) References Cited

U.S. PATENT DOCUMENTS

| 4,940,805 | A  | * | 7/1990 | Fischer | .............. C07C 29/177 |
|---|---|---|---|---|---|
|  |  |  |  |  | 549/326 |
| 7,329,330 | B2 |  | 2/2008 | Gall et al. |  |
| 7,497,931 | B2 | * | 3/2009 | Funke | .................... B01D 3/141 |
|  |  |  |  |  | 203/1 |

(Continued)

FOREIGN PATENT DOCUMENTS

| CN | 102190559 A | 9/2011 |
|---|---|---|
| CN | 102596347 A | 7/2012 |

(Continued)

OTHER PUBLICATIONS

"Pinch Analysis: Part 1." Separation Technologies, Mar. 21, 2012, seperationtechnology.com/pinch-analysis-part-1/. (Year: 2012).*

(Continued)

*Primary Examiner* — Bobby Ramdhanie
*Assistant Examiner* — Briana M Obenhuber
(74) *Attorney, Agent, or Firm* — Dentons US LLP

(57) ABSTRACT

The present application relates to a device and a method for preparing alkanol. According to the present application, energy can be reduced when preparing alkanol by reducing the amount of steam used in a reboiler or cooling water used in a condenser, and steam generated from a heat exchanger for overhead stream can be utilized in a variety of fields. Also, highly pure alkanol can be prepared according to the present application.

22 Claims, 14 Drawing Sheets

(56) References Cited

U.S. PATENT DOCUMENTS

| | | |
|---|---|---|
| 7,594,981 B2 | 9/2009 | Ikeda |
| 8,771,479 B2 | 7/2014 | Lee et al. |
| 2003/0106786 A1* | 6/2003 | Kaibel ............... B01D 3/14 203/74 |
| 2004/0000473 A1 | 1/2004 | Hofen et al. |
| 2005/0252761 A1 | 11/2005 | Funke et al. |
| 2006/0021911 A1 | 2/2006 | Adrian et al. |
| 2010/0193348 A1 | 8/2010 | Heydrich et al. |
| 2011/0041549 A1 | 2/2011 | Van DerSchrick |
| 2011/0303526 A1* | 12/2011 | Lee ............... B01D 3/14 203/81 |
| 2012/0267233 A1 | 10/2012 | Lee et al. |
| 2015/0041308 A1 | 2/2015 | Lee et al. |

FOREIGN PATENT DOCUMENTS

| | | |
|---|---|---|
| JP | 46-34018 B | 10/1971 |
| JP | 58-55002 A | 4/1983 |
| JP | 2005-535728 A | 11/2005 |
| JP | 2008-137996 A | 6/2008 |
| JP | 2012-515771 A | 7/2012 |
| JP | 2012-533424 A | 12/2012 |
| KR | 1020030042465 A | 5/2003 |
| KR | 2003-0088211 A | 11/2003 |
| KR | 1020050089329 A | 9/2005 |
| KR | 1020100085845 A | 7/2010 |
| KR | 1020110008589 A | 1/2011 |
| WO | 2004/073841 A1 | 9/2004 |
| WO | 2008116542 A1 | 10/2008 |

OTHER PUBLICATIONS

"Pinch Analysis: Part 2." Separation Technologies, Apr. 12, 2012, seperationtechnology.com/pinch-analysis-part-1/. (Year: 2012).*

* cited by examiner

【Figure 1】
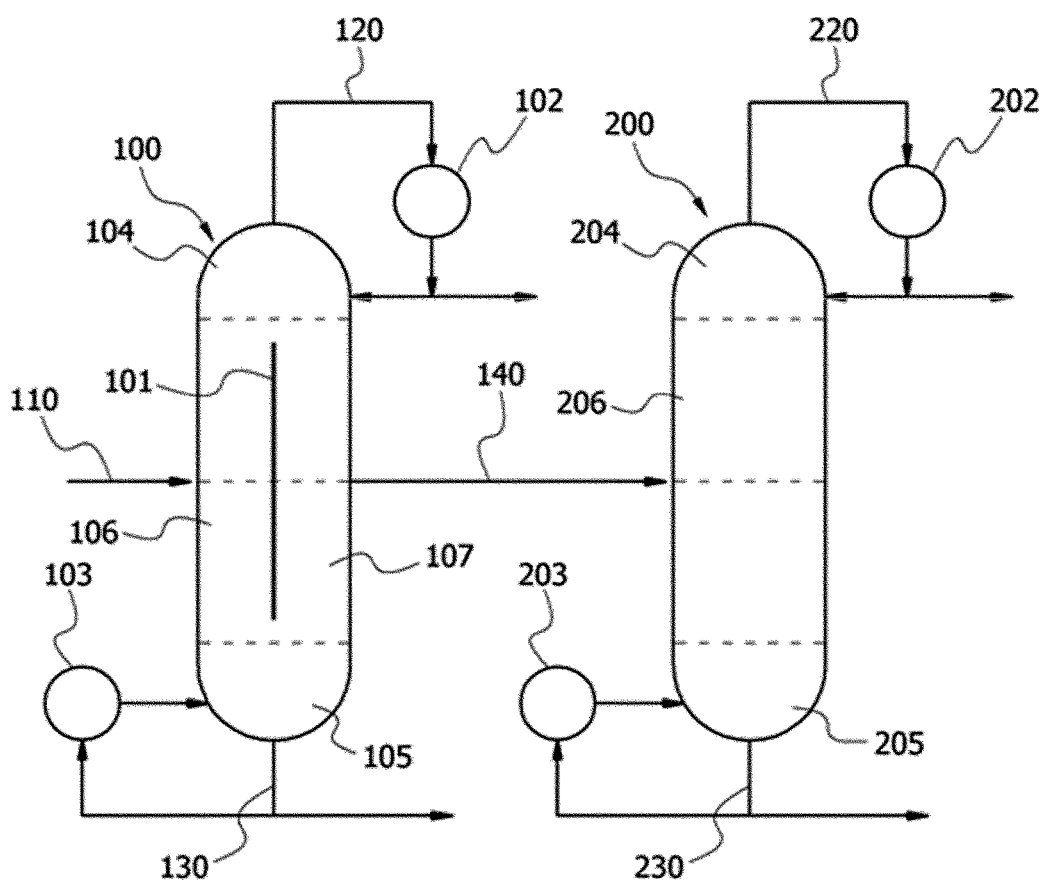

【Figure 2】
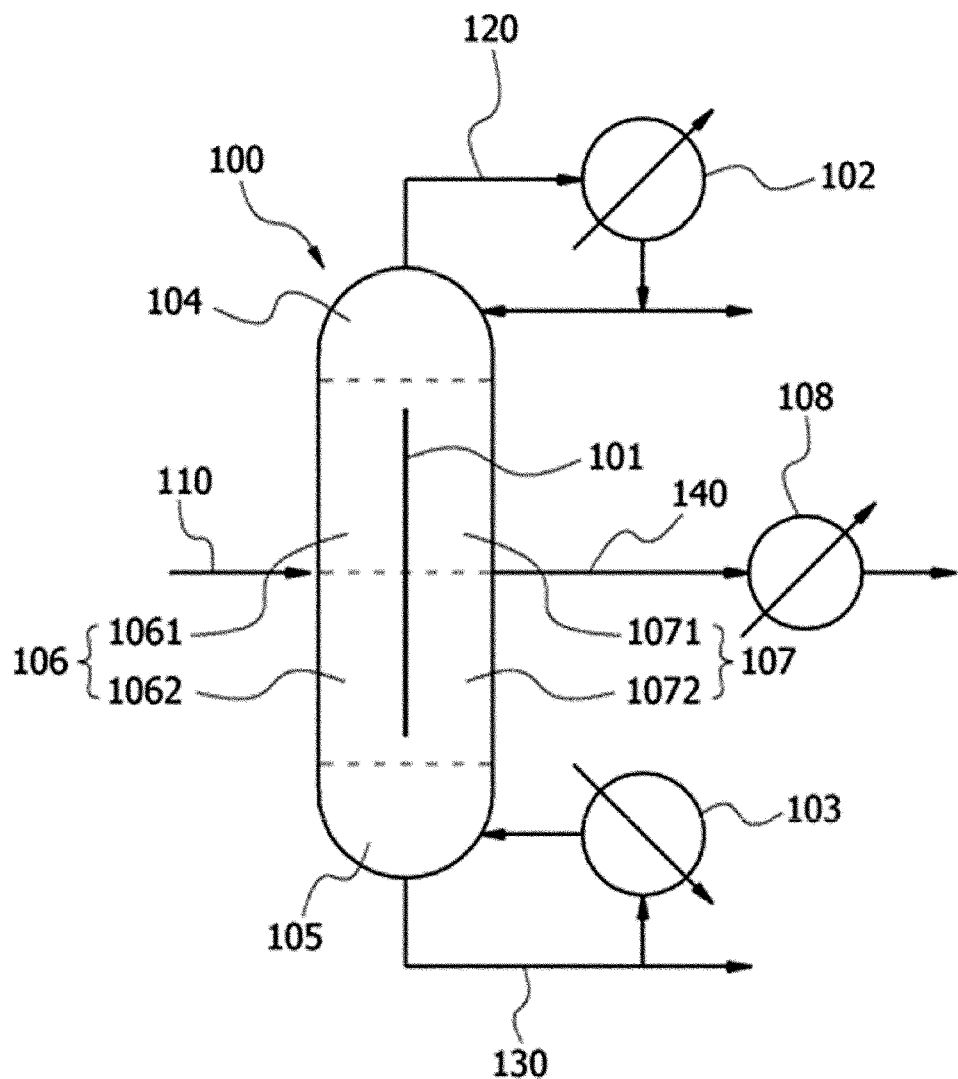

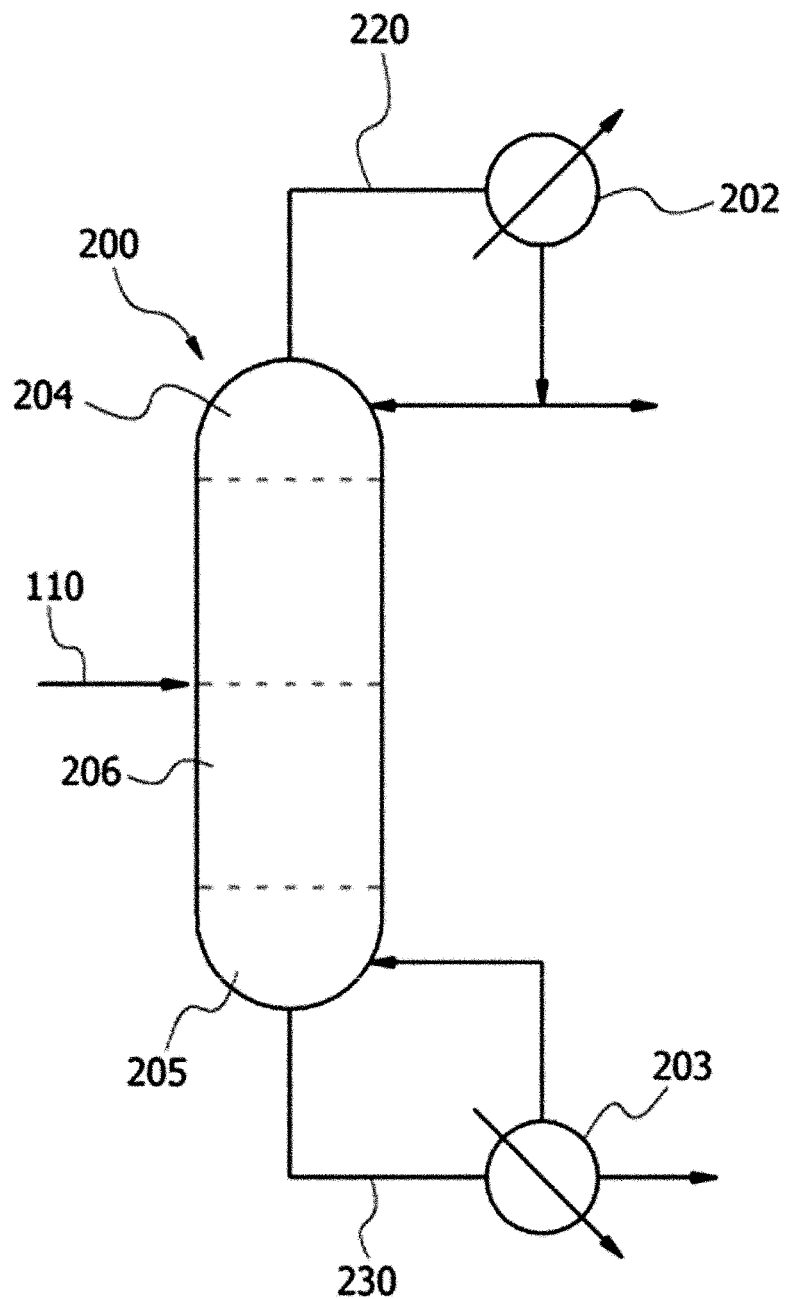
[Figure 3]

【Figure 4】
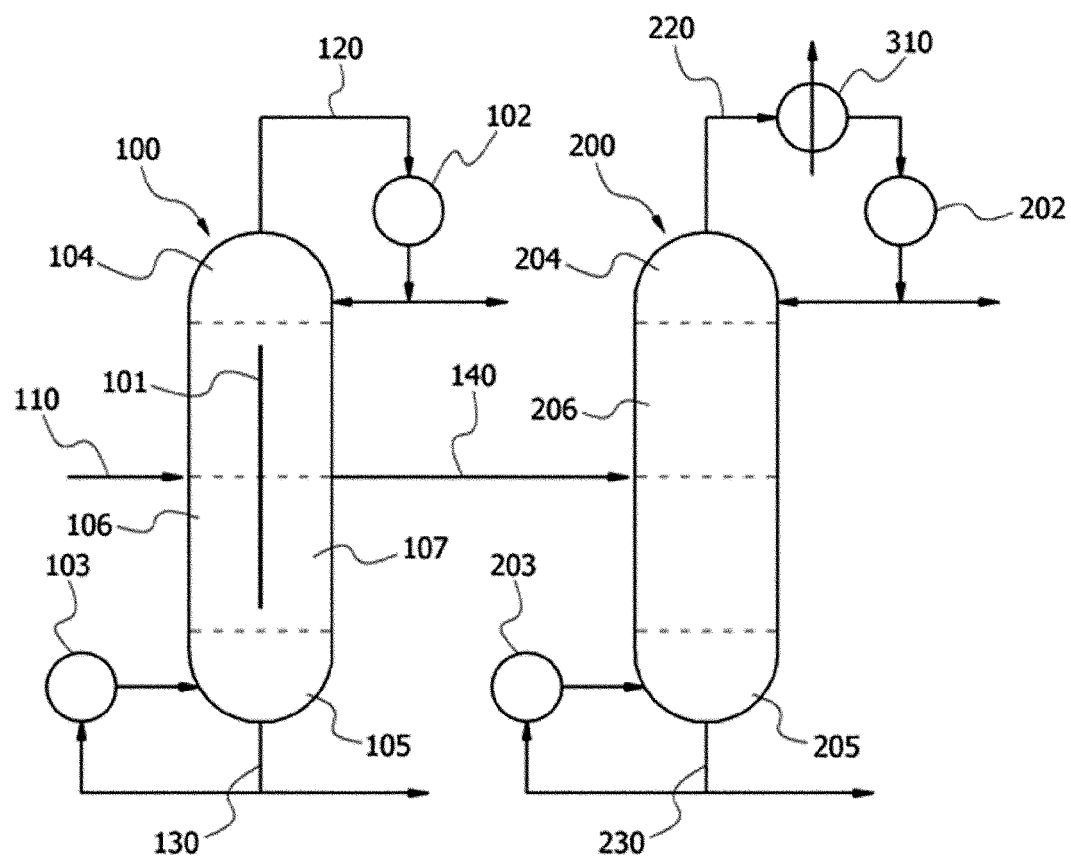

【Figure 5】
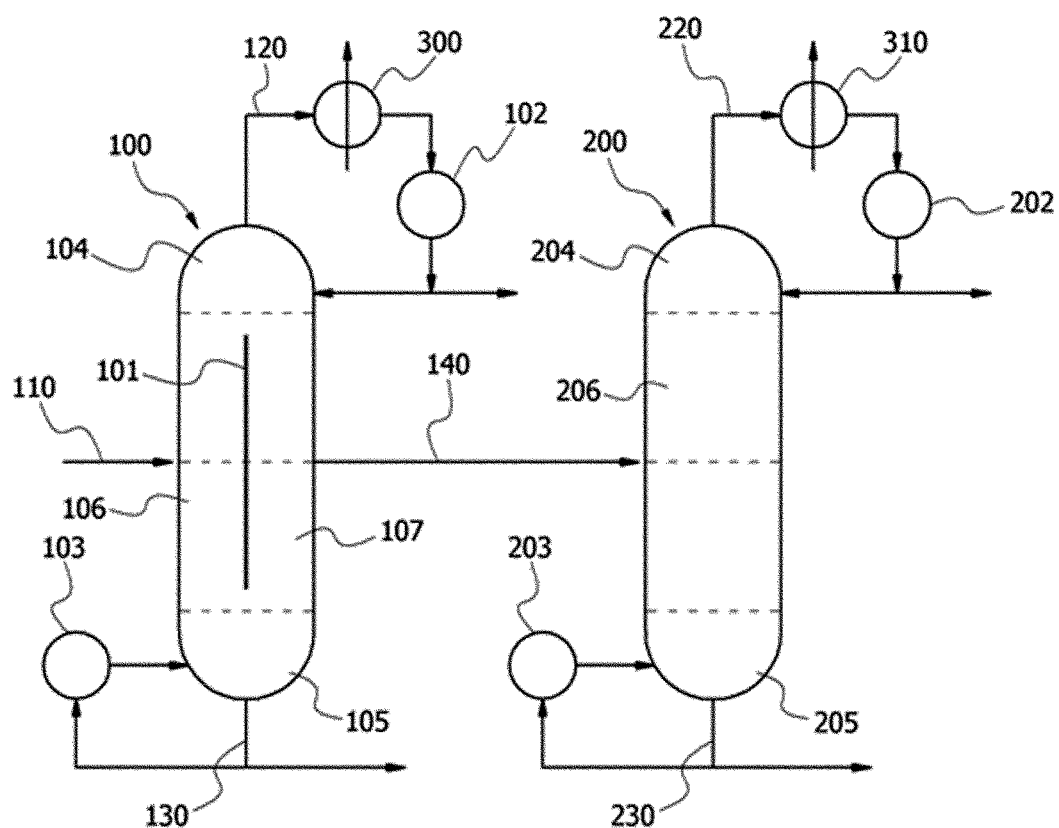

【Figure 6】
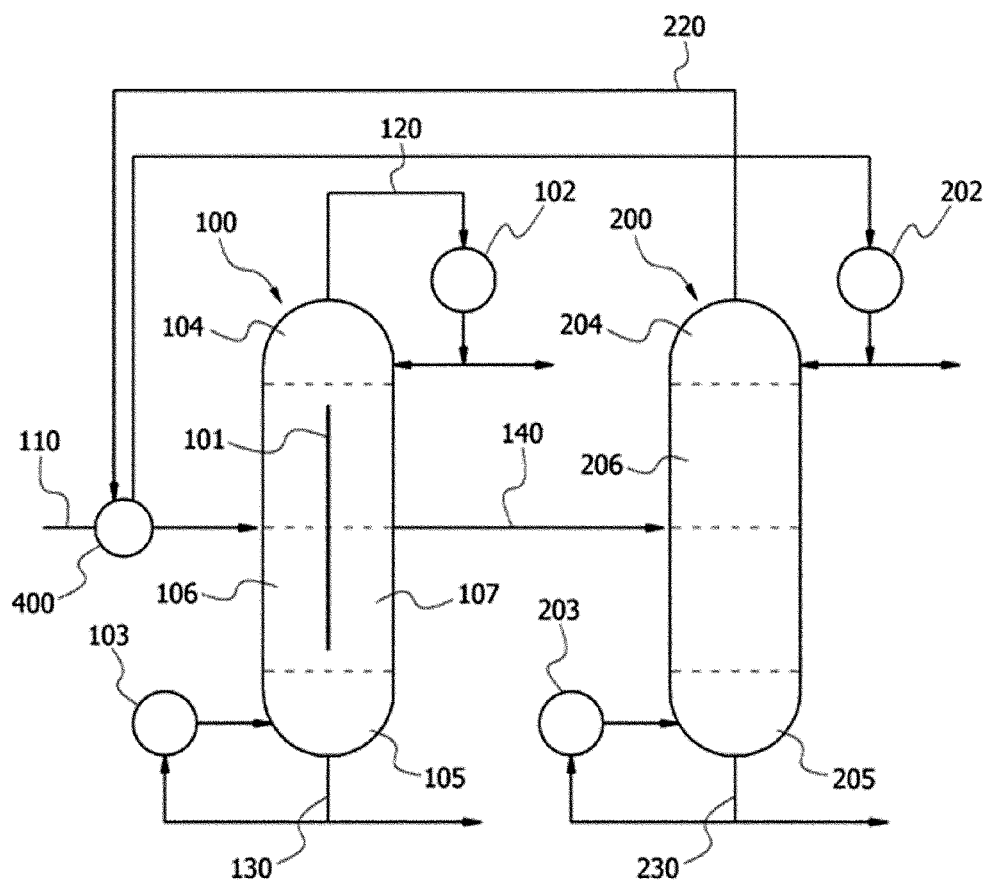

【Figure 7】
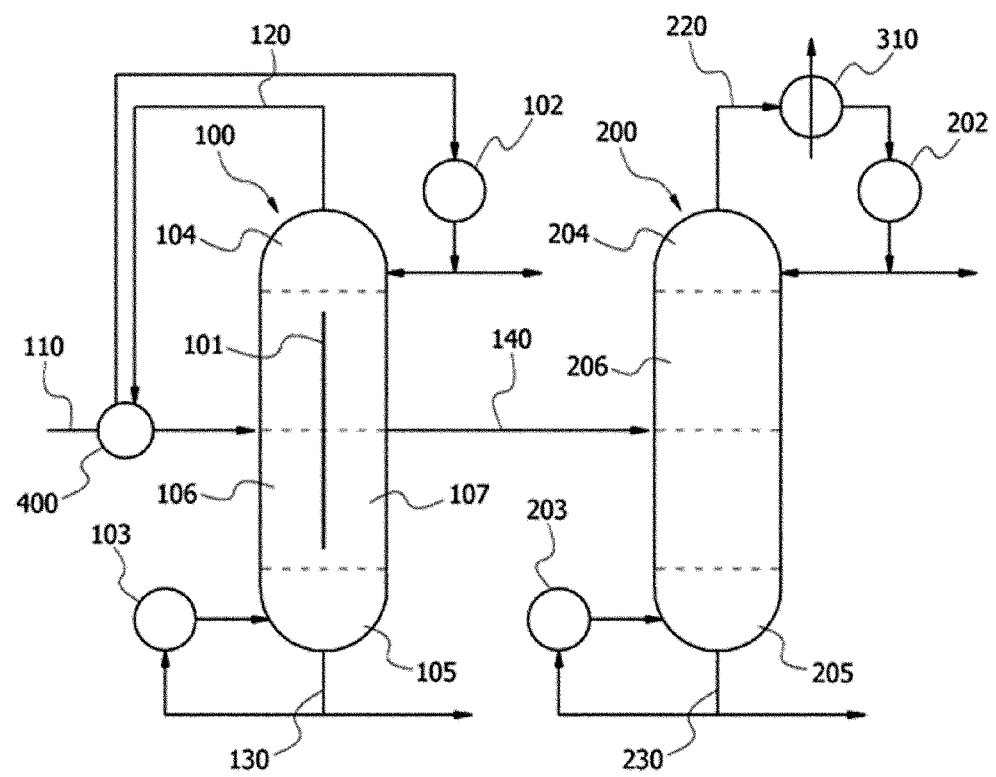

【Figure 8】
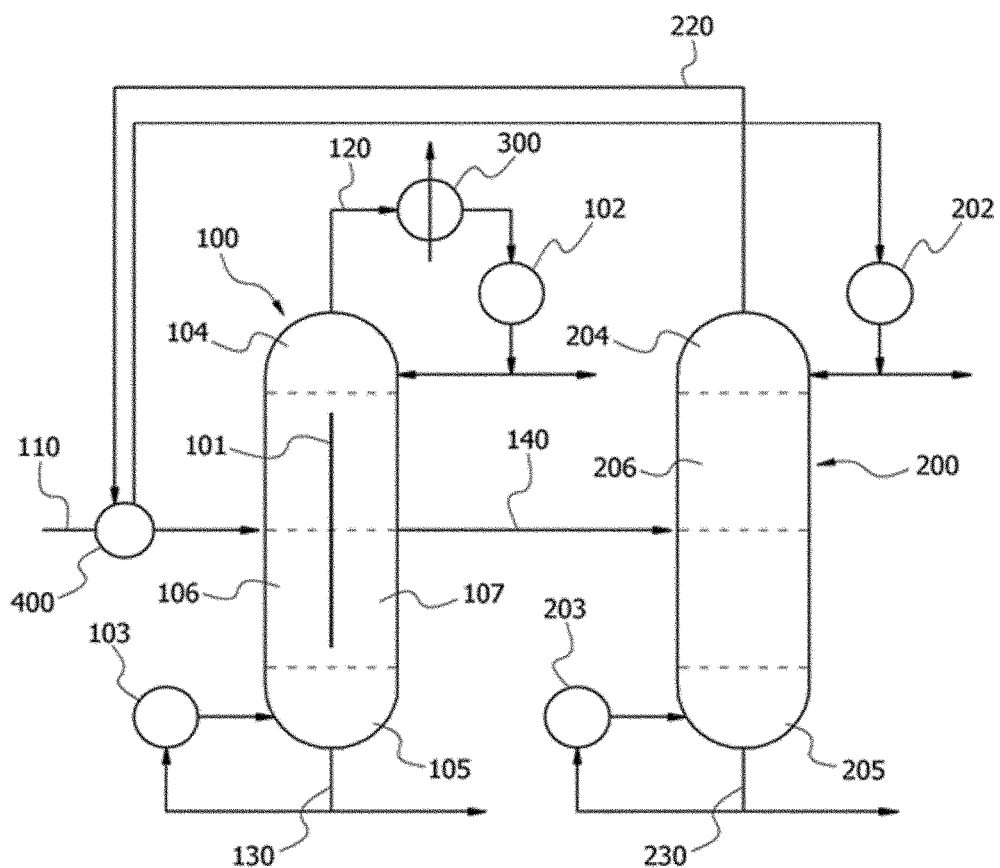

【Figure 9】
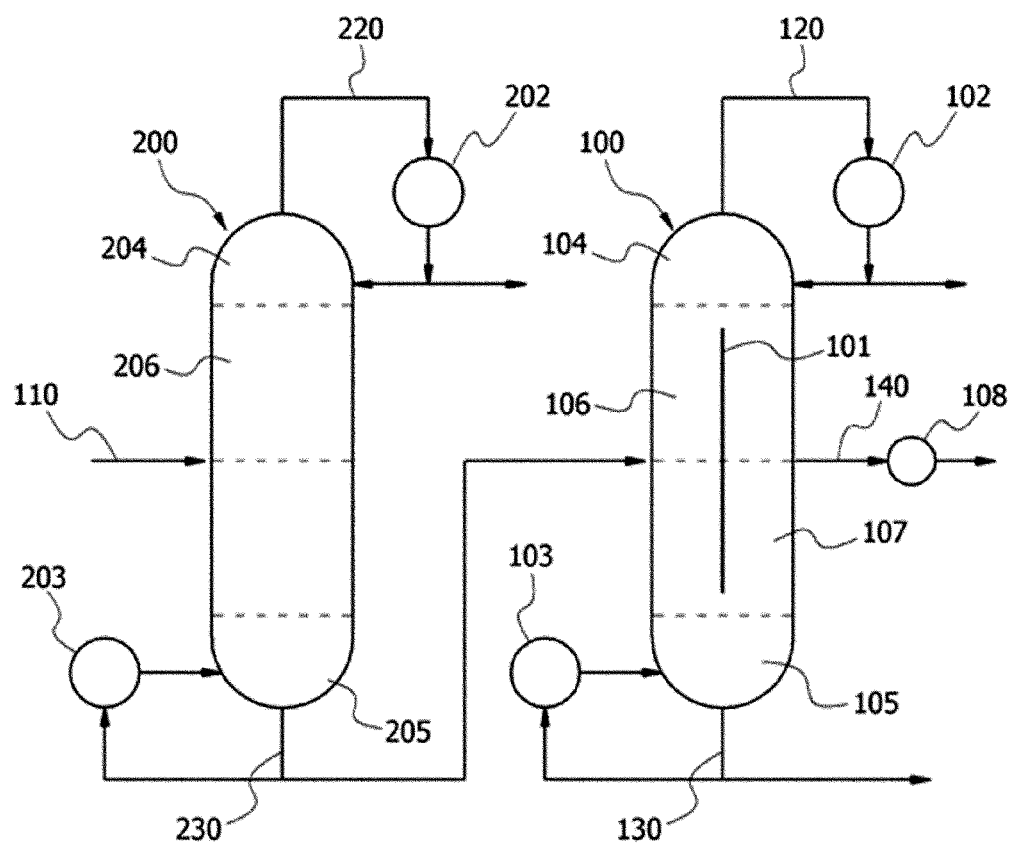

[Figure 10]
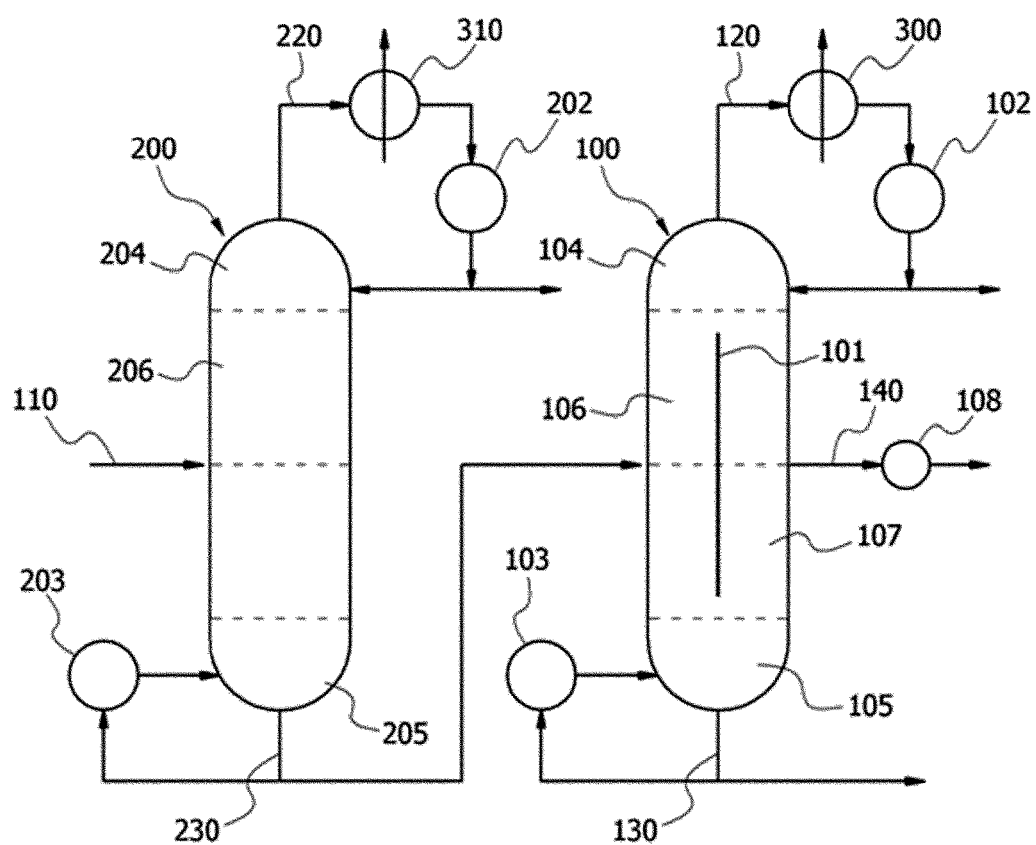

[Figure 11]
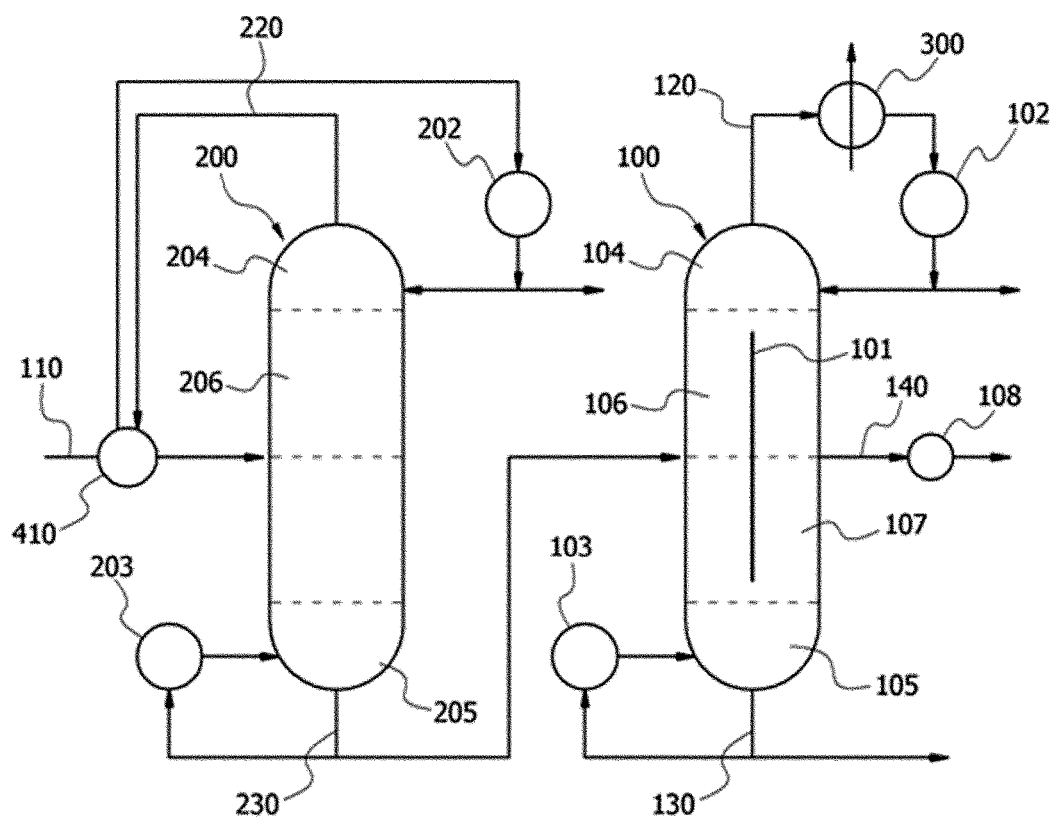

[Figure 12]
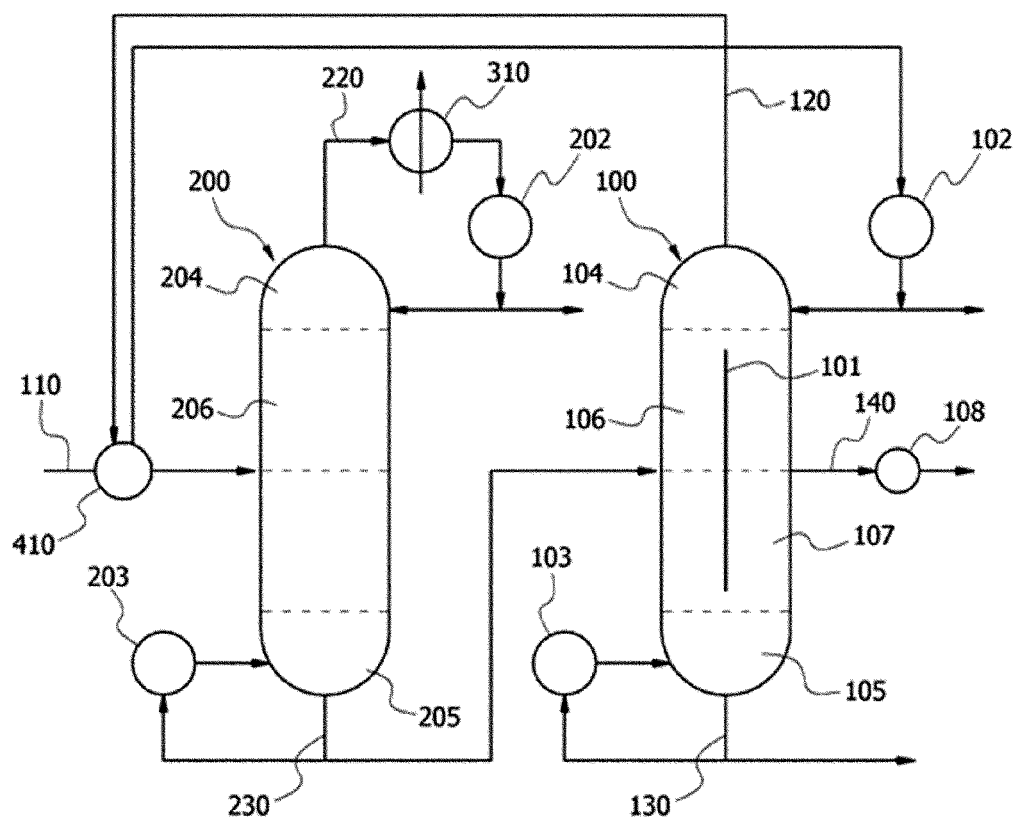

[Figure 13]
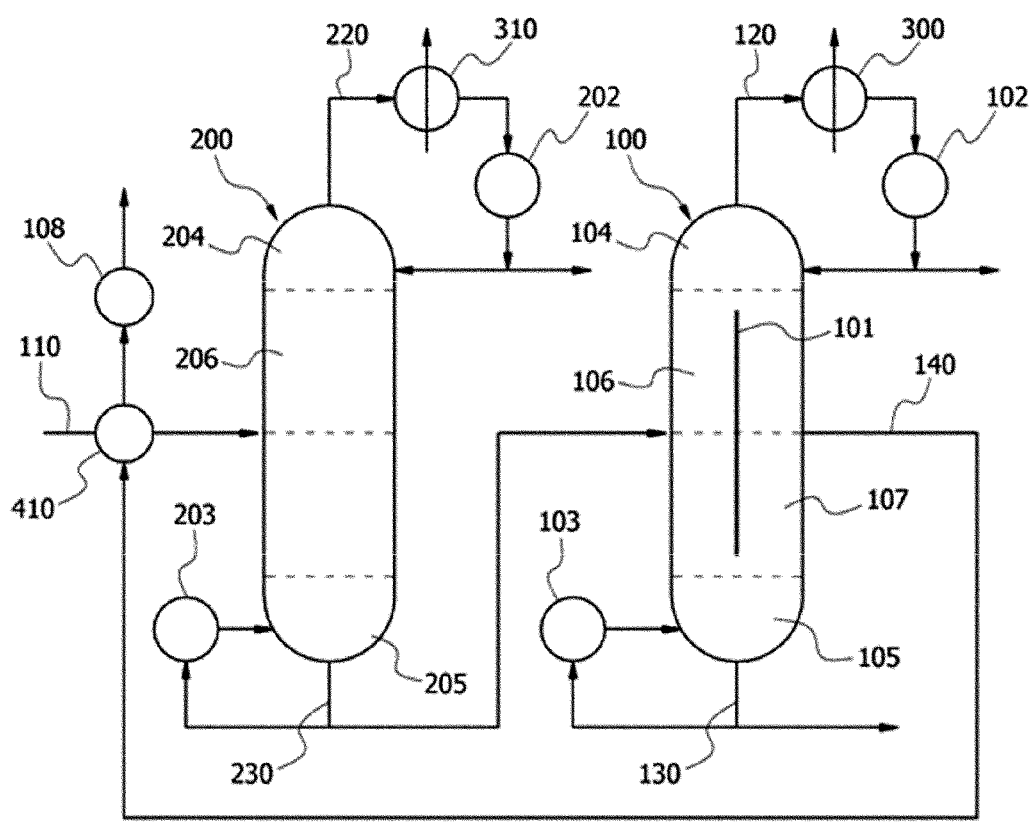

【Figure 14】
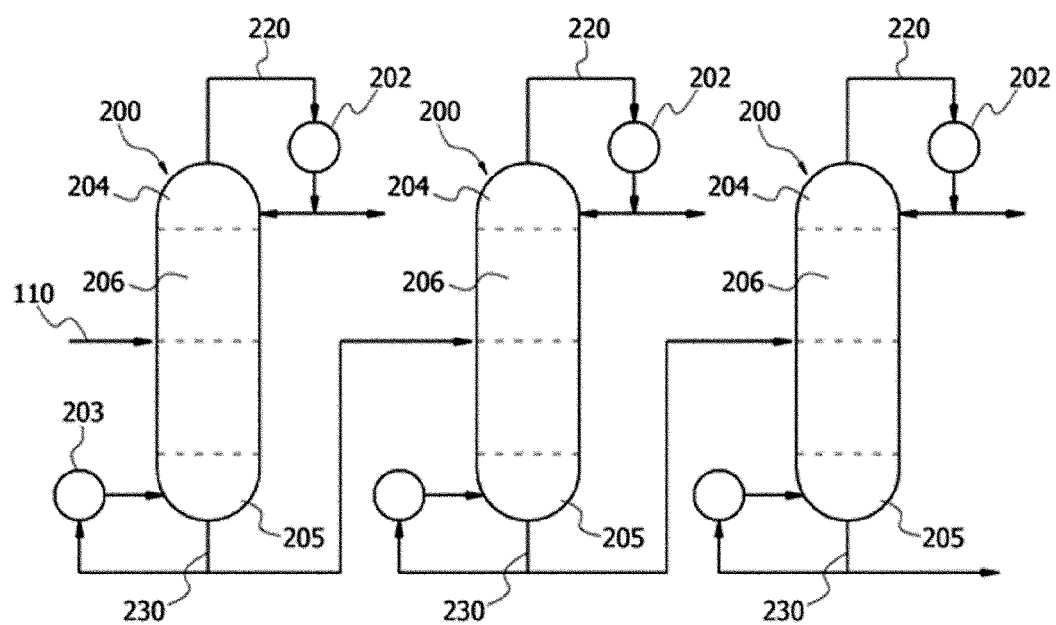

DEVICE FOR PREPARING N-BUTANOL

This application is a National Stage Application of International Application No. PCT/KR2014/000483 filed on Jan. 16, 2014, and claims the benefit of Korean Patent Application No. 10-2013-0004944, filed on Jan. 16, 2013, and Korean Patent Application No. 10-2014-0005344, filed on Jan. 16, 2014, all of which are hereby incorporated by reference in their entirety for all purposes as if fully set forth herein.

TECHNICAL FIELD

The present application relates to a device and a method for preparing an alkanol.

BACKGROUND ART

Alkanols such as n-butanol have, for example, been used for various applications in chemical industry such as solvents upon preparation of a coating solution.

For example, n-butanol may be prepared by hydrogenating n-butylaldehyde. For example, butylaldehyde may be prepared by subjecting a mixed gas of propylene, carbon monoxide (CO), and hydrogen ($H_2$) to an oxo reaction. Typically, the prepared butylaldehyde may be a mixture of n-butylaldehyde and iso-butylaldehyde, and thus n-butanol may be prepared by separating n-butylaldehyde from the mixture, and subjecting the n-butylaldehyde to a hydrogenation reaction.

DISCLOSURE

Technical Problem

The present application is directed to providing a device and a method for preparing an alkanol.

DESCRIPTION OF DRAWINGS

FIG. 1 is a diagram showing an exemplary device for preparing an alkanol.

FIG. 2 is a diagram showing an exemplary divided-wall distillation column.

FIG. 3 is a diagram showing an exemplary general-type distillation column.

FIGS. 4 to 13 are diagrams showing exemplary embodiments of the exemplary device for preparing an alkanol.

FIG. 14 is a diagram showing a device for preparing an alkanol used in Comparative Example 1.

TECHNICAL SOLUTION

One aspect of the present application provides a device for preparing an alkanol. The exemplary preparing device may include a divided-wall distillation column and a general-type distillation column. For example, the device for preparing an alkanol may be a distillation column assembly or a distillation system having the divided-wall distillation column and the general-type distillation column connected thereto, and may be used to separate and refine a high-purity alkanol while minimizing the loss of energy caused in a process of preparing an alkanol. Hereinafter, the device will be described with reference to the accompanying drawings. However, it should be understood that the drawings are shown herein for illustration only, and are not construed as limiting the scope of the device according to one exemplary embodiment of the present application.

FIG. 1 is a diagram showing a device for preparing an alkanol according to a first exemplary embodiment of the present application, that is, a device including a divided-wall distillation column 100 in which a raw material 110 including a compound represented by the following Formula 1 and an isomer thereof flows, and a general-type distillation column 200 which is sequentially connected to the divided-wall distillation column 100 and in which a stream of a product in the divided-wall distillation column 100 flows. The divided-wall distillation column 100 and the general-type distillation column 200 of the device are connected by means of a connection route, for example, a piping system.

R—OH  [Formula 1]

In Formula 1, R represents an alkyl group, for example, an alkyl group having 1 to 20 carbon atoms, 1 to 16 carbon atoms, 1 to 12 carbon atoms, 1 to 8 carbon atoms, or 1 to 6 carbon atoms. The alkyl group may have a linear, branched or cyclic structure, and may be optionally substituted with one or more substituents, when necessary.

According to one exemplary embodiment, the component of Formula 1 may be n-butanol, and the isomer of the component of Formula 1 may be iso-butanol. Also, the product may be a mixture of n-butanol and iso-butanol.

In the foregoing, the divided-wall distillation column 100 is generally a device designed to distill the raw material 110 including three components having a low boiling point, a middle boiling point and a high boiling point. The divided-wall distillation column 100 is generally a device similar to a Petlyuk distillation column in a thermodynamic aspect. The Petlyuk distillation column has a structure in which a preliminary separator and a main separator are thermally integrated. The distillation column is designed so that a low boiling point material and a high boiling point material can be primarily separated at the preliminary separator, components present in column top and column bottom regions of the preliminary separator can flow into a feed stage of the main separator, and the low boiling point material, the middle boiling point material, and the high boiling point material can be separated at the main separator. In this case, the divided-wall distillation column 100 is configured to install a divided wall 101 in the column so as to integrate the preliminary separator into the inside of the main separator.

The divided-wall distillation column 100 may, for example, have a structure as shown in FIG. 2. FIG. 2 shows an exemplary divided-wall distillation column 100. As shown in FIG. 2, the exemplary distillation column may have a structure in which an inner part of the distillation column 100 is divided by a divided wall 101 and which has a divided-type column condenser 102 and a divided-type column reboiler 103 formed respectively in upper and lower portions thereof. Also, the inner part of the divided-wall distillation column 100 may be imaginarily divided by dotted lines shown in FIG. 2, for example, divided into a divided-type column top region 104 from which a high boiling point stream is discharged, a divided-type column bottom region 105 from which a low boiling point stream is discharged, a divided-type column raw material feed region 106 in which the raw material 110 flows, and a product outflow region 107 from which a product flows out. In addition, the divided-type column raw material feed region 106 may be divided into an upper feed region 1061 and a lower feed region 1062, and the product outflow region 107 may be divided into an upper outflow region 1071 and a lower outflow region 1072. In the foregoing, the term "upper and lower feed regions" may refer to upper and lower regions, respectively, when the divided-type column raw material feed region 106, that is, a space in a side of the divided-wall distillation column 100 in which the raw material 110 is fed in spaces divided by the divided wall 101 in the structure of the divided-wall distillation column 100, is bisected in a longitudinal direction of the distillation column. Also, the term "upper and lower outflow regions" may refer to upper and lower regions, respectively, when the product outflow region 107, that is, a space in a side of the divided-wall distillation column 100 from which a product flows out in the spaces divided by the divided wall 101 in the inner part of the divided-wall distillation column 100.

Specific types of the divided-wall distillation column 100 that may be used in a process of distilling an alkanol are not particularly limited. For example, the divided-wall distillation column 100 having a typical structure as shown in FIG. 2 may be used, or a distillation column designed so that the position and shape of the divided wall 101 in the distillation column are altered in consideration of refining efficiency may also be used. Also, the plate number and internal diameter of the distillation column are not particularly limited, and may, for example, determined based on a theoretical plate number derived from a distillation curve plotted in consideration of compositions of the raw material 110.

In the foregoing, the general-type distillation column 200 is a device in which a multi-component material included in the raw material 110 may be separated by a difference in boiling points of components. The term "general-type distillation column" used herein refers to a distillation column which has no divided wall 101 present therein and is not the divided-wall distillation column 100. In the present application, distillation columns having various shapes may be used in consideration of the boiling points of the component of the raw material 110 flowing therein, or the components to be separated. The exemplary general-type distillation column 200 may be typically configured as shown in FIG. 3. Referring to FIG. 3, the exemplary general-type distillation column 200 may have a structure having a general-type column condenser 202 and a general-type column reboiler 203 formed in upper and lower portions thereof. Also, an inner part of the general-type distillation column 200 may, for example, be divided into a general-type column top region 204 from which the low boiling point stream is discharged, a general-type column bottom region 205 from which the high boiling point stream is discharged, and a general-type column raw material feed region 206 in which the raw material 110 flows. When the raw material 110 is introduced into the general-type column raw material feed region 206 of the general-type distillation column 200 as described above, steam evaporated at the reboiler in the distillation column rises upward in the distillation column, and a liquid condensed in the condenser is refluxed, and flows downward in the distillation column. When the liquid comes in contact with the steam in the distillation column, the steam condenses and the liquid evaporates. In this case, since the component having a low boiling point has a strong tendency to evaporate, and the component having a high boiling point has a strong tendency to condense, the concentration of the low boiling point component increases as the component rises upward in the distillation column. Therefore, pure steam of the low boiling point component may be obtained in an upper portion of the distillation column. In this case, the steam condenses in the general-type column condenser 202, and some of the low boiling point component is produced as a product, and the remaining low boiling point component is refluxed again. The refluxed solution is used to condense the high boiling point component rising upward in the distillation column and return the high boiling point component to a bottom of the distillation column. Also, some of the high boiling point component discharged from a lower portion of the distillation column may also be produced as a product, and the remaining high boiling point component may evaporate in the general-type column reboiler 203, and transferred to a lower stage of the distillation column. Here, the high boiling point component may be used to evaporate the components in the distillation column. The term "condenser" used herein may refer to a device installed at a channel of a piping system separately from the main body of the device, that is, a cooling device configured to cool a material flowing out from the main body with cooling water using a method of bringing the material in contact with the cooling water. Also, the term "reboiler" may, for example, refer to a heating device installed outside a refining column such as a distillation column, or an evaporation device configured to again heat and evaporate a product, extracted from the bottom of the refining column, in which the components having a high boiling point is rich.

According to one exemplary embodiment, to perform a refining process on the raw material 110 including three components having a low boiling point, a middle boiling point and a high boiling point, the divided-wall distillation column 100 and the general-type distillation column 200 may be connected through a piping system so that the raw material 110 including the compound of Formula 1 and isomer thereof flows in the divided-type column raw material feed region 106 of the divided-wall distillation column 100, and a product stream 140 in the divided-wall distillation column 100 is introduced into the general-type distillation column 200 as a raw material, as shown in FIG. 1. In this case, a component having a relatively low boiling point in the components of the raw material 110 may be discharged from the divided-type column top region 104 of the divided-wall distillation column 100 as a divided-type column top stream 120, and some of the discharged divided-type column top stream 120 may be refluxed to the divided-wall distillation column 100 through the divided-type column condenser 102. A component having a relatively high boiling point in the components of the raw material 110 may be discharged from the column bottom region 105 of the divided-wall distillation column 100 as a divided-type column bottom stream 130, and some of the discharged divided-type column bottom stream 130 may be refluxed to the divided-wall distillation column 100 through the divided-type column reboiler 103. Also, the product stream 140 having the middle boiling point component may be discharged from the product outflow region 107 of the divided-wall distillation column 100, and then introduced into the general-type column raw material feed region 206 of the general-type distillation column 200 connected to the divided-wall distillation column 100. As a similar separation process is performed in the general-type distillation column 200, a component having a relatively low boiling point may be discharged into the general-type column top region 204 as a general-type column top stream 220, and some of the discharged general-type column top stream 220 may be refluxed to the general-type distillation column 200 through the general-type column condenser 202. Also, a component having a relatively high boiling point may be discharged into the general-type column bottom region 205 as a general-type column bottom stream 230, and some of the discharged general-type column bottom stream 230 may be refluxed to the general-type distillation column 200 through the general-type column reboiler 203. For example, when the raw material 110 including n-butanol and an isomer thereof (i.e., iso-butanol) flows into the divided-wall distillation column 100, the components having relatively low and high boiling points are separated in the divided-type column top region 104 and the divided-type column bottom region 105 of the divided-wall distillation column 100, and discharged as the divided-type column top stream 120 and the divided-type column bottom stream 130, respectively. Also, the product stream 140 including the middle boiling point components such as iso-butanol and n-butanol is discharged from the product outflow region 107, for example, the upper outflow region 1071 or the lower outflow region 1072, of the divided-wall distillation column 100, and flows into the general-type column raw material feed region 206 of the general-type distillation column 200 connected to the divided-wall distillation column 100. Then, iso-butanol that is a component having a relatively low boiling point flows out from the general-type column top region 204 of the general-type distillation column 200, and n-butanol that is a component having a relatively high boiling point flows out from the general-type column bottom region 205. In the foregoing, the divided-type column top stream 120 of the divided-wall distillation column 100, and the general-type column top stream 220 of the general-type distillation column 200 may be refluxed to the divided-type column top region 104 and the general-type column top region 204 through the divided-type column condenser 102 and the general-type column condenser 202, respectively, or may be stored as products. Also, the divided-type column bottom stream 130 of the divided-wall distillation column 100, and the general-type column bottom stream 230 of the general-type distillation column 200 may be refluxed to the divided-type column bottom region 105 and the general-type column bottom region 205 through the divided-type column reboiler 103 and the general-type column reboiler 203, respectively, or may be stored as articles. The "column top stream" used herein refers to a stream, discharged from the divided-type column top region 104 of the divided-wall distillation column 100 or the general-type column top region 204 of the general-type distillation column 200, in which the low boiling point component having a relatively low boiling point is rich, and the term "column bottom stream" refers to a stream, discharged from the divided-type column bottom region 105 of the divided-wall distillation column 100 or the general-type column bottom region 205 of the general-type distillation column 200, in which the high boiling point component having a relatively high boiling point is rich. In the foregoing, the term "product stream" also refers to a stream of a product flowing out from the product outflow region 107 of the divided-wall distillation column 100, that is, a stream in which the middle boiling point component is rich. In the foregoing, the term "rich stream" refers to a stream in which the low boiling point component included in the stream discharged from the column top region, the high boiling point component included in the stream discharged from the column bottom region, and the middle boiling point component included in the stream discharged from the product outflow region have higher contents than the low boiling point component, the high boiling point component, and the middle boiling point component included in the raw material 110, respectively. For example, the rich stream may refer to a stream in which each of the low boiling point component, the high boiling point component, and the middle boiling point component included in the stream discharged from the column top region, the column bottom region, and the product outflow region has a content of 50% by weight or more, 80% by weight or more, 90% by weight or more, 95% by weight or more, or 99% by weight or more. In this specification, the low boiling point stream and the column top stream may be used synonymously, the high boiling point stream and the column bottom stream may be used synonymously, and the middle boiling point stream and the product stream may be used synonymously.

FIGS. 4 and 5 are diagrams showing preparing devices according to second and third exemplary embodiments of the present application. Here, the preparing device may include a heat exchanger which is arranged at a front stage(s) of the divided-type column condenser and/or the general-type column condenser, and configured such that some or all of at least one of inflow and outflow streams in the divided-wall distillation column and the general-type distillation column may exchange heat. For example, in the heat exchanger, some or all of at least one of the divided-type column top stream and the general-type column top stream may exchange heat with external water at the front stage(s) of the divided-type column condenser and/or the general-type column condenser, or, in the heat exchanger, some or all of at least one of the divided-type column top stream and the general-type column top stream may exchange heat with the raw material flowing into the divided-type column raw material feed region at the front stage(s) of the divided-type column condenser and/or the general-type column condenser so as to raise a temperature of the raw material.

According to one exemplary embodiment of the present application, the heat exchanger may be a heat exchanger 300 or 310 for producing steam. In the foregoing, the heat exchanger 300 or 310 for producing steam may be arranged to be directly or indirectly coupled to a connection route of the preparing device. In a thermodynamic aspect, the heat exchanger 300 or 310 for producing steam may be preferably directly coupled to a pipe through which the divided-type column top stream 120 or the general-type column top stream 220 flows. Also, the heat exchanger 300 or 310 for producing steam may, for example, be arranged at a front stage of the condenser 102 or 202 so that at least one of the divided-type column top stream 120 and the column top stream in the general-type distillation column 200 sequentially passes through the heat exchanger 300 or 310 and the condenser 102 or 202. For example, as shown in FIG. 5, after at least one of the divided-type column top stream 120 and the general-type column top stream 220 sequentially passes through the heat exchanger 300 for producing steam, and the divided-type column condenser 102, some of the divided-type column top stream 120 passing through the divided-type column condenser 102 may be refluxed to the divided-wall distillation column 100, or, after at least one of the divided-type column top stream 120 and the general-type column top stream 220 sequentially passes through the heat exchanger 310 for producing steam, and the general-type column condenser 202, some of the general-type column top stream 220 passing through the general-type column condenser 202 may be refluxed to the general-type distillation column 200.

Since the preparing device further includes the heat exchanger 300 or 310 for producing steam as described above, at least one of the divided-type column top stream 120 and the general-type column top stream 220 passes through the heat exchanger 300 or 310 for producing steam. In this case, heat is applied to the heat exchanger 300 or 310 for producing steam. Therefore, the divided-type column top stream 120 and the general-type column top stream 220 are refluxed to the divided-wall distillation column 100 and the general-type distillation column 200 at a relatively low temperature, respectively. In this case, the cost spent in a condensation process in which the condenser 102 or 202 is used may be cut by reducing the quantity of cooling water used in the condensation process before the divided-type column top stream 120 and the general-type column top stream 220 are refluxed to the divided-wall distillation column 100 and the general-type distillation column 200, respectively.

In the exemplary preparing device, at least one of the divided-type column top stream 120 and the general-type column top stream 220 passes through the heat exchanger 300 or 310 for producing steam. In the heat exchanger 300 or 310 for producing steam, at least one of the divided-type column top stream 120 and the general-type column top stream 220 may exchange heat with external water to produce a high-temperature steam. The high-temperature steam produced in the heat exchanger 300 or 310 for producing steam may, for example, be used as a heat source in a vaporizer, a stripping column, or an isomer column used in a process of preparing butanol. According to one exemplary embodiment, when the general-type column top stream exchanges heat with external water as shown in FIG. 4, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 13 to 20. Also, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 10 to 50, more preferably 13 to 25. According to one exemplary embodiment, when both of the divided-type column top stream and the general-type column top stream exchange heat with external water as shown in FIG. 5, the divided-type column top stream 120 refluxed to the divided-wall distillation column 100 after the heat exchange is completed may also have a reflux ratio of 1 to 100. In a thermodynamic aspect, the reflux ratio of the divided-type column top stream 120 may be preferably in a range of 10 to 60, more preferably 15 to 23. Also, the general-type column top stream 220 refluxed to the general-type distillation column 200 after the heat exchange is completed may also have a reflux ratio of 1 to 100. In a thermodynamic aspect, the reflux ratio of the general-type column top stream 220 may be preferably in a range of 10 to 50, more preferably 13 to 25. When the reflux ratio of the divided-type column top stream 120 is adjusted in a range of 100 or less, preferably 19 or less, as described above, the energy consumed to reflux the divided-type column top stream 120, which exchanges heat with water by means of the heat exchanger 300 for producing steam and is then refluxed to the divided-wall distillation column 100 at a temperature of 100 to 120° C., may be minimized, and some of the divided-type column top stream 120 may be simultaneously produced as a high-purity product. Also, when the reflux ratio of the general-type column top stream 220 is adjusted in a range of 100 or less, preferably 21 or less, as described above, the energy consumed to reflux the general-type column top stream 220, which exchanges heat with water by means of the heat exchanger 310 for producing steam and is then refluxed to the general-type distillation column 200 at a temperature of 100 to 120° C., may be minimized, and some of the general-type column top stream 220 may be simultaneously produced as a high-purity product. The "reflux ratio" used herein refers to a ratio of a flow rate of a refluxed stream with respect to an outflow rate of a stream flowing out from the distillation column.

FIGS. 6 to 8 are diagrams showing preparing devices according to fourth, fifth, and sixth exemplary embodiments of the present application.

According to still another exemplary embodiment of the present application, the heat exchanger may be a heat exchanger 400 for preheating a raw material, as shown in FIGS. 6 to 8. As shown in FIGS. 6 to 8, the heat exchanger 400 for preheating a raw material may be arranged to be directly or indirectly coupled to a connection route of the preparing device. In a thermodynamic aspect, the heat exchanger for preheating a raw material may be preferably directly coupled to a pipe through which the column top stream in the divided-wall or general-type distillation column 200, and the raw material 110 flowing into the divided-wall distillation column 100 flow. Also, the heat exchanger 400 for preheating a raw material may, for example, be arranged at a front stage of the condenser 102 or 202 so that at least one of the divided-type column top stream 120 and the general-type column top stream 220 sequentially passes through the heat exchanger 400 for preheating a raw material, and the condenser 102 or 202. For example, after at least one of the divided-type column top stream 120, and the column top stream 220 in the general-type distillation column 200 sequentially passes through the heat exchanger 400 for preheating a raw material, and the divided-type column condenser 102, some of the divided-type column top stream 120 passing through the divided-type column condenser 102 may be refluxed to the divided-wall distillation column 100, or, after at least one of the divided-type column top stream 120, and the column top stream 220 in the general-type distillation column 200 sequentially passes through the heat exchanger 400 for preheating a raw material, and the general-type column condenser 202, some of the general-type column top stream 220 passing through the general-type column condenser 202 may be refluxed to the general-type distillation column 200.

As described above, when the preparing device further includes the heat exchanger 400 for preheating a raw material, at least one of the divided-type column top stream 120 and the general-type column top stream 220 passes through the heat exchanger 400 for preheating a raw material. In this case, heat is applied to the heat exchanger 400 for preheating a raw material. Therefore, some of the divided-type column top stream 120 and the general-type column top stream 220 are refluxed to the divided-wall distillation column 100 and the general-type distillation column 200 at a relatively low temperature, respectively, and the rest of the separate and general-type column top stream 120 and 220 may be produced as products. As described above, as at least one of the divided-type column top stream 120 and the general-type column top stream 220 exchanges heat with the low-temperature raw material 110 flowing into the divided-wall distillation column 100, the at least one of the divided-type column top stream 120 and the general-type column top stream 220 may be used to preheat the raw material 110 flowing into the divided-wall distillation column 100. As a result, the energy consumed in a heater configured to raise a temperature of the raw material 110 flowing into the divided-wall distillation column 100, or in the divided-type column reboiler 103 configured to heat the divided-type column bottom stream 130 discharged from the divided-type column bottom region 105 of the divided-wall distillation column 100 may be reduced. Further, the cost spent in a condensation process in which the divided-type column condenser 102 and the general-type column condenser 202 are used may be cut by reducing the quantity of cooling water used in the condensation process before the divided-type column top stream 120 in the divided-wall distillation column 100 is refluxed to the divided-type column top region 104, or the general-type column top stream 220 in the general-type distillation column 200 is refluxed to the general-type column top region 204. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 10 to 18. Also, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 10 to 50, more preferably 10 to 20. When the raw material whose heat exchange is completed by means of the heat exchanger 400 for preheating a raw material and which has a temperature of 50 to 95° C. flows into the divided-wall distillation column 100, and then flows out from the divided-type column top region 104 at a temperature of 95 to 115° C., the energy consumed to reflux the divided-type column top stream 120, which is refluxed to the divided-wall distillation column 100 in the divided-type column top stream 120 flowing out at a temperature of 95 to 115° C., may be minimized, and some of the divided-type column top stream 120 may be simultaneously produced as a high-purity product by adjusting the reflux ratio of the divided-type column top stream 120 in a range of 100 or less, preferably 18 or less, as described above. Also, the energy consumed to reflux the general-type column top stream, which is refluxed to the general-type distillation column 200 in the general-type column top stream 220 which exchanges heat by means of the heat exchanger 400 for preheating a raw material and then flows out from the general-type column top region 204 at a temperature of 95 to 105° C., may be minimized, and some of the general-type column top stream 220 may be produced as a high-purity product by adjusting the reflux ratio of the general-type column top stream 220 in a range of 100 or less, preferably 20 or less, as described above.

As schematically shown in FIG. 7, the preparing device may also include a general-type column heat exchanger 310 for producing steam, and a divided-type column heat exchanger 400 for preheating a raw material. According to one exemplary embodiment, the general-type column heat exchanger 310 for producing steam may be arranged at a piping system through which the general-type column top stream 220 in the general-type distillation column 200 flows, for example, arranged at a front stage of the general-type column condenser 202, the general-type column top stream 220 may pass through the general-type column heat exchanger 310 for producing steam, and then pass through the general-type column condenser 202. Then, some of the general-type column top stream 220 may be refluxed to the general-type distillation column 200. Also, the divided-type column heat exchanger 400 for preheating a raw material may be arranged at a piping system through which the divided-type column top stream 120 in the divided-wall distillation column 100 flows, for example, arranged at a front stage of the divided-type column condenser 102, the divided-type column top stream 120 passes through the divided-type column heat exchanger 400 for preheating a raw material, and then pass through the divided-type column condenser 102. Then, some of the divided-type column top stream 120 may be refluxed to the divided-wall distillation column 100.

The general-type column top stream 220 in the general-type distillation column 200 may pass through the general-type column heat exchanger 310 for producing steam, and exchange heat with external water to produce steam. In this case, the steam produced in the general-type column heat exchanger 310 for producing steam may be used to reduce the energy consumed in a heater configured to raise a temperature of the raw material 110 flowing into the divided-wall distillation column 100, or in the divided-type column reboiler 103 configured to heat the divided-type column bottom stream 130 discharged from the divided-type column bottom region 105 of the divided-wall distillation column 100. The divided-type column top stream 120 in the divided-wall distillation column 100 may pass through the divided-type column heat exchanger 400 for preheating a raw material, and exchange heat with the raw material 110 flowing into the divided-type column raw material feed region 106 so as to preheat the raw material 110. Since the preparing device includes the general-type column heat exchanger 310 for producing steam, and the divided-type column heat exchanger 400 for preheating a raw material, the steam produced in the general-type column heat exchanger 310 for producing steam may be used in various fields, and an effect of cutting the cost consumed in a condensation process in which the general-type column condenser 202 is used may be achieved by reducing the quantity of cooling water used in the condensation process before the general-type column top stream 220 is refluxed to the general-type column top region 204. At the same time, as the divided-type column top stream 120 exchanges heat with the raw material 110 flowing into the divided-wall distillation column 100 in the divided-type column heat exchanger 400 for preheating a raw material, an effect of cutting the cost consumed in a condensation process in which the divided-type column condenser 102 is used may be further achieved by reducing the quantity of cooling water used in the condensation process before the overhead stream in the divided-wall distillation column 100 is refluxed to the divided-wall distillation column 100. Also, the energy consumed in a heater configured to raise a temperature of the raw material 110 flowing into the divided-wall distillation column 100, or in the divided-type column reboiler 103 configured to heat the divided-type column bottom stream 130 discharged from the divided-type column bottom region 105 of the divided-wall distillation column 100 may be reduced. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 12 to 20. Also, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 10 to 50, more preferably 13 to 25. When the reflux ratio of the divided-type column top stream 120 is adjusted in a range of 100 or less, preferably 18.5 or less, as described above, the energy consumed to reflux the divided-type column top stream, which is refluxed to the divided-wall distillation column 100 in the divided-type column top stream 120 which exchanges heat by means of the divided-type column heat exchanger 400 for preheating a raw material and has a temperature of 90 to 100° C., may be minimized, and some of the divided-type column top stream 120 may be simultaneously produced as a high-purity product. Also, when the reflux ratio of the general-type column top stream 220 is adjusted in a range of 100 or less, preferably 21 or less, as described above, the energy consumed to reflux the general-type column top stream 220, which exchanges heat with water by means of the general-type column heat exchanger 310 for producing steam and is then refluxed to the general-type distillation column 200 at a temperature of 100 to 120° C., may be minimized, and some of the general-type column top stream 220 may be simultaneously produced as a high-purity article.

As shown in FIG. 8, the preparing device may also include a divided-type column heat exchanger 300 for producing steam, and the divided-type column heat exchanger 400 for preheating a raw material. According to one exemplary embodiment, since the divided-type column heat exchanger 300 for producing steam may be arranged at a piping system through which the divided-type column top stream 120 in the divided-wall distillation column 100 flows, for example, arranged at a front stage of the divided-type column condenser 102, the divided-type column top stream 120 may pass through the divided-type column heat exchanger 300 for producing steam, and then pass through the divided-type column condenser 102. Then, some of the divided-type column top stream 120 may be refluxed to the divided-wall distillation column 100. Also, the divided-type column heat exchanger 400 for preheating a raw material may be arranged at a piping system through which the general-type column top stream 220 in the general-type distillation column 200 flows, for example, arranged at a front stage of the general-type column condenser 202, the general-type column top stream 220 may pass through the divided-type column heat exchanger 400 for preheating a raw material, and then pass through the general-type column condenser 202. Then, some of the general-type column top stream 220 may be refluxed to the general-type distillation column 200.

The divided-type column top stream 120 in the divided-wall distillation column 100 may pass through the divided-type column heat exchanger 300 for producing steam, and exchange heat with external water to produce steam. For example, the steam produced in the divided-type column heat exchanger 300 for producing steam may be used in a heating process in which the heater is used before the raw material 110 is allowed to flow into the divided-wall distillation column 100. The general-type column top stream 220 in the general-type distillation column 200 may pass through the divided-type column heat exchanger 400 for preheating a raw material, and exchange heat with the raw material 110 flowing into the divided-type column raw material feed region 106 so as to preheat the raw material 110. When the preparing device includes the divided-type column heat exchanger 300 for producing steam, and the divided-type column heat exchanger 400 for preheating a raw material, the steam produced in the divided-type column heat exchanger 300 for producing steam may be used in various fields, and an effect of cutting the cost consumed in a condensation process in which the divided-type column condenser 102 is used may be achieved by reducing the quantity of cooling water used in the condensation process before the divided-type column top stream 120 is refluxed to the divided-type column top region 104. At the same time, as the general-type column top stream 220 exchanges heat with the raw material 110 flowing into the divided-wall distillation column 100 in the divided-type column heat exchanger 400 for preheating a raw material, an effect of cutting the cost consumed in a condensation process in which the general-type column condenser 202 is used may be further achieved by reducing the quantity of cooling water used in the condensation process before the overhead stream in the general-type distillation column 200 is refluxed to the general-type distillation column 200. Also, the energy consumed in a heater configured to raise a temperature of the raw material 110 flowing into the divided-wall distillation column 100, or in the divided-type column reboiler 103 configured to heat the divided-type column bottom stream 130 discharged from the divided-type column bottom region 105 of the divided-wall distillation column 100 may be reduced. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 11 to 19. Also, the general-type column top stream 220 refluxed to the general-type distillation column 200 after the heat exchange is completed may have a reflux ratio of 1 to 100. In a thermodynamic aspect, the reflux ratio of general-type column top stream 220 may be preferably in a range of 10 to 50, more preferably 12 to 25. When the reflux ratio of the divided-type column top stream 120 is adjusted in a range of 100 or less, preferably 17.5 or less, as described above, the energy consumed to reflux the divided-type column top stream 120, which exchanges heat with water by means of the divided-type column heat exchanger 300 for producing steam and is then refluxed to the divided-wall distillation column 100 at a temperature of 100 to 120° C., may be minimized, and some of the divided-type column top stream 120 may be simultaneously produced as a high-purity product. Also, when the reflux ratio of the general-type column top stream 220 is adjusted in a range of 100 or less, preferably 20.8 or less, as described above, the energy consumed to reflux the general-type column top stream, which is refluxed to the general-type distillation column 200 in the general-type column top stream 220 which exchanges heat by means of the divided-type column heat exchanger 400 for preheating a raw material and has a temperature of 90 to 105° C., may be minimized, and some of the general-type column top stream 220 may be simultaneously produced as a high-purity product.

Although not shown, the device for preparing an alkanol according to one exemplary embodiment of the present application may also include at least two divided-type column heat exchangers for preheating a raw material. For example, when the preparing device includes two divided-type column heat exchangers for preheating a raw material, the divided-type column top stream may exchange heat with a low-temperature raw material flowing into a low-temperature divided-wall distillation column by means of a first divided-type column heat exchanger for preheating a raw material so as to preheat the raw material flowing into the divided-wall distillation column. When the raw material is not sufficiently preheated, the general-type column top stream and the raw material may be further preheated by means of a second divided-type column heat exchanger for preheating a raw material. According to one exemplary embodiment, the first divided-type column heat exchanger for preheating a raw material may be arranged at a piping system through which the divided-type column top stream of the divided-wall distillation column flows, for example, arranged at a front stage of the divided-type column condenser, so that the divided-type column top stream may pass through the first divided-type column heat exchanger for preheating a raw material, and then pass through the divided-type column condenser. Then, some of the divided-type column top stream may be refluxed to the divided-wall distillation column. Also, the second divided-type column heat exchanger for preheating a raw material may be arranged at a piping system through which the general-type column top stream of the general-type distillation column flows, for example, arranged at a front stage of the general-type column condenser, so that the general-type column top stream may pass through the divided-type column heat exchanger for preheating a raw material, and then pass through the general-type column condenser. Then, some of the general-type column top stream may be refluxed to the general-type distillation column. Therefore, the energy consumed in a heater configured to raise a temperature of the raw material flowing into the divided-wall distillation column, or a reboiler configured to heat a column bottom stream discharged from a column bottom region of the divided-wall distillation column may be reduced. Further, the cost spent in a condensation process in which the divided-type column condenser is used may be cut by reducing the quantity of cooling water used in the condensation process before the low boiling point stream in the divided-wall distillation column is refluxed to the divided-type column top region of the divided-wall distillation column. According to one exemplary embodiment, the temperature of the divided-type column top stream and the general-type column top stream may be regulated so that a difference in temperature ($\Delta T_{min}$) between the divided-type or general-type column top stream and the raw material preheated by means of the divided-type column heat exchanger for preheating a raw material is greater than or equal to 5° C. For example, the difference in temperature ($\Delta T_{min}$) may be regulated by pressurizing or depressurizing the pipe through which the divided-type column top stream or the general-type column top stream flows. In this case, the divided-type column top stream refluxed to the divided-wall distillation column after the heat exchange is completed may also have a reflux ratio of 1 to 100. In a thermodynamic aspect, the reflux ratio of the divided-type column top stream may be preferably in a range of 10 to 60, more preferably 10.5 to 18.5. Also, the general-type column top stream refluxed to the general-type distillation column after the heat exchange is completed may also have a reflux ratio of 1 to 100. In a thermodynamic aspect, the reflux ratio of the general-type column top stream may be preferably in a range of 10 to 50, more preferably 11.8 to 25. When the reflux ratio of the divided-type column top stream is adjusted in a range of 100 or less, preferably 17 or less, as described above, the energy consumed to reflux the divided-type column top stream, which is refluxed to the divided-wall distillation column in the divided-type column top stream which exchanges heat by means of the first divided-type column heat exchanger for preheating a raw material and has a temperature of 95 to 115° C., may be minimized, and some of the divided-type column top stream may be simultaneously produced as a high-purity product. Also, when the reflux ratio of the general-type column top stream is adjusted in a range of 100 or less, preferably 21 or less, as described above, the energy consumed to reflux the general-type column top stream, which is refluxed to the general-type distillation column in the general-type column top stream which exchanges heat by means of the second divided-type column heat exchanger for preheating a raw material and has a temperature of 100 to 120° C., may be minimized, and some of the general-type column top stream may be simultaneously produced as a high-purity product.

FIG. 9 is a diagram showing an exemplary device for preparing an alkanol according to a seventh exemplary embodiment of the present application.

As shown in FIG. 9, to perform a refining process on the raw material 110 including three components having a low boiling point, a middle boiling point and a high boiling point according to still another exemplary embodiment of the present application, the divided-wall distillation column 100 and the general-type distillation column 200 may be generally coupled through a piping system so that the raw material 110 including the compound of Formula 1 and isomer thereof flows into the general-type column raw material feed region 206 of the general-type distillation column 200, and the general-type column bottom stream 230 in the general-type distillation column 200 is introduced into the divided-type column raw material feed region 106 of the divided-wall distillation column 100 as a raw material, as shown in FIG. 9. In this case, water and a component having a relatively low boiling point in the components of the raw material 110 are discharged from the general-type column top region 204 of the general-type distillation column 200 as the general-type column top stream 220, and some of the discharged general-type column top stream 220 may be refluxed to the general-type distillation column 200 through the general-type column condenser 202. A component having a relatively high boiling point in the components of the raw material 110, and the stream including the compound of Formula 1 and isomer thereof may be discharged from the general-type column bottom region 205 of the general-type distillation column 200 as the general-type column bottom stream 230, and some of the discharged general-type column bottom stream 230 may be refluxed to the general-type distillation column 200 through the general-type column reboiler 203. Also, the rest of the general-type column bottom stream 230 may be introduced into the divided-type column raw material feed region 106 of the divided-wall distillation column 100 connected to the general-type distillation column 200. As a similar separation process is performed in the divided-wall distillation column 100, a component having a relatively low boiling point may be discharged into the divided-type column top region 104 as the divided-type column top stream 120, and some of the discharged divided-type column top stream 120 may be refluxed to the divided-wall distillation column 100 through the divided-type column condenser 102. Also, a component having a middle boiling point may flow out from the product outflow region 107, a component having a high boiling point may be discharged into the divided-type column bottom region 105 as the divided-type column bottom stream 130, and some of the discharged divided-type column bottom stream 130 may be refluxed to the divided-wall distillation column 100 through the divided-type column reboiler 103. For example, when the raw material 110 including n-butanol and an isomer thereof (i.e., iso-butanol) flows into the general-type column raw material feed region 206 of the general-type distillation column 200, the low boiling point component and the high boiling point component are separated in the general-type column top region 204 and the general-type column bottom region 205 of the general-type distillation column 200, and discharged into the general-type column top stream 220 and the general-type column bottom stream 230, respectively. Also, some of the general-type column bottom stream 230 including the high boiling point component, the iso-butanol and the n-butanol may be refluxed to the general-type distillation column 200 through the general-type column reboiler 203, and the rest of the general-type column bottom stream 230 may flow into the raw material feed region 106 of the divided-wall distillation column 100 connected to the general-type distillation column 200. Then, iso-butanol that is a component having a relatively low boiling point flows out from the divided-type column top region 104 of the divided-wall distillation column 100, n-butanol that is a component having a relatively middle boiling point flows out from the product outflow region 107, and the high boiling point component flows out from the divided-type column bottom region 105. In the foregoing, the general-type column top stream 220 in the general-type distillation column 200, and the divided-type column top stream 120 in the divided-wall distillation column 100 may be refluxed to the general-type column top region 204 and the divided-type column top region 104 through the general-type column condenser 202 and the divided-type column condenser 102, respectively, and may be stored as products. Also, the general-type column bottom stream 230 in the general-type distillation column 200, and the divided-type column bottom stream 130 in the divided-wall distillation column 100 may be refluxed to the general-type column bottom region 205 and the divided-type column bottom region 105 through the general-type column reboiler 203 and the divided-type column reboiler 103, respectively, and may be produced as products.

FIG. 10 is a diagram showing a preparing device according to an eighth exemplary embodiment of the present application.

As shown in FIG. 10, the preparing device may include a heat exchanger arranged at a front stage(s) of the divided-type column condenser and/or the general-type column condenser, and configured such that some or all of at least one of inflow and outflow streams in the divided-wall distillation column and the general-type distillation column may exchange heat. For example, in the heat exchanger, some or all of at least one of the divided-type column top stream and the general-type column bottom stream may exchange heat with external water at the front stage(s) of the divided-type column condenser and/or the general-type column condenser, or some or all of at least one of the divided-type column top stream and the general-type column bottom stream may exchange heat with the raw material flowing into the general-type column raw material feed region at the front stage(s) of the divided-type column condenser and/or the general-type column condenser so as to raise a temperature of the raw material.

According to one exemplary embodiment of the present application, the heat exchanger may be a heat exchanger 300 or 310 for producing steam, as shown in FIG. 10. In the foregoing, the heat exchanger 300 or 310 for producing steam may be arranged to be directly or indirectly coupled to a connection route of the preparing device. In a thermodynamic aspect, the heat exchanger 300 or 310 for producing steam may be preferably directly coupled to a pipe through which the column top stream in the general-type distillation column 200 or the divided-wall distillation column 100 flows. Also, the heat exchanger 300 or 310 for producing steam may, for example, arranged at the front stage of the condenser 102 or 202 so that at least one of the general-type column top stream 220 and the divided-type column top stream 120 sequentially passes through the heat exchanger 300 or 310 for producing steam, and the condenser 102 or 202. For example, after the at least one of the general-type column top stream 220 and the divided-type column top stream 120 sequentially passes through the heat exchanger 310 for producing steam, and the general-type column condenser 202, some of the general-type column top stream 220 passing through the general-type column condenser 202 may be refluxed to the general-type distillation column 200, or after the at least one of the general-type column top stream 220 and the divided-type column top stream 120 sequentially passes through the heat exchanger 300 for producing steam, and the divided-type column condenser 102, some of the divided-type column top stream 120 passing through the divided-type column condenser 102 may be refluxed to the divided-wall distillation column 100.

Since the preparing device further includes the heat exchanger 300 or 310 for producing steam as described above, at least one of the general-type column top stream 220 and the divided-type column top stream 120 passes through the heat exchanger 300 or 310 for producing steam. In this case, heat is applied to the heat exchanger 300 or 310 for producing steam. Therefore, the general-type column top stream 220 and the divided-type column top stream 120 are refluxed to the general-type distillation column 200 and the divided-wall distillation column 100 at a relatively low temperature, respectively. In this case, the cost spent in a condensation process in which the condenser 102 or 202 is used may be cut by reducing the quantity of cooling water used in the condensation process before the general-type column top stream 220 and the divided-type column top stream 120 are refluxed to the general-type distillation column 200 and the divided-wall distillation column 100, respectively.

In the exemplary preparing device, at least one of the general-type column top stream 220, and the column top stream in the divided-wall distillation column passes through the heat exchanger 300 or 310 for producing steam. In the heat exchanger for producing steam, at least one of the general-type column top stream 220 and the divided-type column top stream 120 may exchange heat with external water to produce high-temperature steam. The high-temperature steam produced in the heat exchanger 300 or 310 for producing steam may, for example, used as a heat source in a vaporizer, a stripping column, or an isomer column used in a process of preparing butanol, as described above. In this case, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 5 to 40, more preferably 6 to 25.5. Also, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 50, more preferably 13.5 to 33.5. When the reflux ratio of the general-type column top stream 220 is adjusted in a range of 100 or less, preferably 10.8 or less, as described above, the energy consumed to reflux the general-type column top stream, which exchanges heat with water by means of the heat exchanger 310 for producing steam and is then refluxed to the general-type distillation column 200 in the general-type column top stream 220 having a temperature of 100 to 120° C., may be minimized, and some of the general-type column top stream 220 may be simultaneously produced as a high-purity product. Also, when the reflux ratio of the divided-type column top stream 120 is adjusted in a range of 100 or less, preferably 20.5 or less, as described above, the energy consumed to reflux the divided-type column top stream 120, which exchanges heat with water by means of the heat exchanger 300 for producing steam and is then refluxed to the divided-wall distillation column 100 in the divided-type column top stream 120 having a temperature of 95 to 125° C., may be minimized, and some of the divided-type column top stream 120 may be simultaneously produced as a high-purity product.

FIGS. 11 and 12 are diagrams showing exemplary preparing devices according to ninth and tenth exemplary embodiments of the present application.

According to still another exemplary embodiment of the present application, the heat exchanger may be a heat exchanger 410 for preheating a raw material, as shown in FIGS. 11 and 12. The heat exchanger 410 for preheating a raw material may be arranged to be directly or indirectly coupled to a connection route of the preparing device. In a thermodynamic aspect, the heat exchanger 410 for preheating a raw material may be preferably directly coupled to a pipe through which the column top stream 120 or 220 in divided-wall distillation column 210 or the general-type distillation column 200, and the raw material 110 flowing into the general-type distillation column 200 flow. Also, the heat exchanger 410 for preheating a raw material may, for example, be arranged at a front stage of the condenser 102 or 202 so that at least one of the general-type column top stream 220 and the divided-type column top stream 120 sequentially passes through the heat exchanger 410 and the condenser 102 or 202. For example, after at least one of the general-type column top stream 220 and the divided-type column top stream 120 sequentially passes through the heat exchanger 410 for preheating a raw material, and the general-type column condenser 202, some of the general-type column top stream 220 passing through the general-type column condenser 202 may be refluxed to the general-type distillation column 200, as shown in FIG. 11, or after at least one of the general-type column top stream 220 and the divided-type column top stream 120 sequentially passes through the heat exchanger 410 for preheating a raw material, and the divided-type column condenser 102, some of the divided-type column top stream 120 passing through the divided-type column condenser 102 may be refluxed to the divided-wall distillation column 100, as shown in FIG. 12.

When the preparing device further includes the heat exchanger 410 for preheating a raw material as described above, at least one of the general-type column top stream 220 and the divided-type column top stream 120 passes through the heat exchanger 410 for preheating a raw material. In this case, heat is applied to the heat exchanger 410 for preheating a raw material. Therefore, some of the general-type column top stream 220 and the divided-type column top stream 120 may be refluxed to the general-type distillation column 200 and the divided-wall distillation column 100 at a relatively low temperature, respectively, and the remaining general-type and divided-type column top streams 220 and 120 may be produced as products. As at least one of the general-type column top stream 220 and the divided-type column top stream 120 exchanges heat with the low-temperature raw material 110 flowing into the general-type distillation column 200 as described above, the raw material 110 flowing into the general-type distillation column 200 may be preheated. Therefore, the energy consumed in a heater configured to raise a temperature of the raw material 110 flowing into the general-type distillation column 200, or in the general-type column reboiler 203 configured to heat the general-type column bottom stream 230 discharged from the general-type column bottom region 205 of the general-type distillation column 200 may be reduced. Further, the cost spent in a condensation process in which the general-type column condenser 202 and the divided-type column condenser 102 are used may be cut by reducing the quantity of cooling water used in the condensation process before the general-type column top stream 220 is refluxed to the general-type column top region 204, or the divided-type column top stream 120 is refluxed to the divided-type column top region 104. In this case, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 5 to 40, more preferably 3 to 20. Also, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 50, more preferably 13 to 33. When the reflux ratio of the general-type column top stream 220 is adjusted in a range of 100 or less, preferably 9.3 or less, as described above, the energy consumed to reflux the general-type column top stream, which is refluxed to the general-type distillation column 200 in the general-type column top stream 220 which exchanges heat by means of the general-type column heat exchanger 410 for preheating a raw material and has a temperature of 90 to 115° C., may be minimized, and some of the general-type column top stream 220 may be simultaneously produced as a high-purity product. Also, when the raw material whose heat exchange is completed by means of the general-type column heat exchanger 410 for preheating a raw material flows into the general-type distillation column 200, and some of the general-type column bottom stream 230 flowing out from the general-type column bottom region 205 at a temperature of 115 to 140° C. then flows into the divided-wall distillation column 100, the energy consumed to reflux the divided-type column top stream, which is refluxed to the divided-wall distillation column 100 in the divided-type column top stream 120 having a temperature of 105 to 120° C., may be minimized, and some of the divided-type column top stream 120 may be simultaneously produced as a high-purity product by adjusting the reflux ratio of the divided-type column top stream 120 in a range of 100 or less, preferably 20.5 or less, as described above.

As schematically shown in FIG. 11, the preparing device may also include the divided-type column heat exchanger 300 for producing steam, and the general-type column heat exchanger 410 for preheating a raw material. According to one exemplary embodiment, the divided-type column heat exchanger 300 for producing steam may be arranged at a piping system through which the divided-type column top stream 120 in the divided-wall distillation column 100 flows, for example, arranged at a front stage of the divided-type column condenser 102, so that the divided-type column top stream 120 may pass through the divided-type column heat exchanger 300 for producing steam, and then pass through the divided-type column condenser 102. Then, some of the divided-type column top stream 120 may be refluxed to the divided-wall distillation column 100. Also, the general-type column heat exchanger 410 for preheating a raw material may be arranged at a piping system through which the general-type column top stream 220 in the general-type distillation column 200, and the raw material 110 flowing into the general-type distillation column 200 flow, for example, arranged at a front stage of the general-type column condenser 202, so that the general-type column top stream 220 may pass through the general-type column heat exchanger 410 for preheating a raw material, and then pass through the general-type column condenser 202. Then, some of the general-type column top stream 220 may be refluxed to the general-type distillation column 200.

The divided-type column top stream 120 may pass through the divided-type column heat exchanger 300 for producing steam, and exchange heat with external water to produce steam, and the steam produced in the divided-type column heat exchanger 300 for producing steam may, for example, be used in a heating process in which the heater is used before the raw material 110 is allowed to flow in the divided-wall distillation column 100. The general-type column top stream 220 may pass through the general-type column heat exchanger 410 for preheating a raw material, and exchange heat with the raw material 110 flowing into the general-type column raw material feed region 206 so as to preheat the raw material 110. When the preparing device includes the divided-type column heat exchanger 300 for producing steam, and the general-type column heat exchanger 410 for preheating a raw material, the steam produced in the divided-type column heat exchanger 300 for producing steam may be used in various fields, and an effect of cutting the cost consumed in a condensation process in which the divided-type column condenser 102 is used may be achieved by reducing the quantity of cooling water used in the condensation process before the divided-type column top stream 120 is refluxed to the divided-type column top region 104. At the same time, as the general-type column top stream 220 exchanges heat with the raw material 110 flowing into the general-type distillation column 200 in the general-type column heat exchanger 410 for preheating a raw material, an effect of cutting the cost consumed in a condensation process in which the general-type column condenser 202 is used may be further achieved by reducing the quantity of cooling water used in the condensation process before the overhead stream in the general-type distillation column 200 is refluxed to the general-type distillation column 200. Also, the energy consumed in a heater configured to raise a temperature of the raw material 110 flowing into the general-type distillation column 200, or in the general-type column reboiler 203 configured to heat the general-type column bottom stream 230 discharged from the general-type column bottom region 205 of the general-type distillation column 200 may be reduced. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 13 to 33. Also, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 10 to 50, more preferably 3 to 20. When the reflux ratio of the general-type column top stream 220 is adjusted in a range of 100 or less, preferably 9.3 or less, as described above, the energy consumed to reflux the general-type column top stream, which is refluxed to the general-type distillation column 200 in the general-type column top stream 220 which exchanges heat by means of the general-type column heat exchanger 410 for preheating a raw material and has a temperature of 90 to 115° C., may be minimized, and some of the general-type column top stream 220 may be simultaneously produced as a high-purity product 6. Also, when the reflux ratio of the divided-type column top stream 120 is adjusted in a range of 100 or less, preferably 20.5 or less, as described above, the energy consumed to reflux the divided-type column top stream, which is refluxed to the divided-wall distillation column 100 in the divided-type column top stream 120 which exchanges heat with water by means of the divided-type column heat exchanger 300 for producing steam and has a temperature of 105 to 120° C., may be minimized, and some of the divided-type column top stream 120 may be simultaneously produced as a high-purity product.

As shown in FIG. 12, the preparing device may also include the general-type column heat exchanger 310 for producing steam, and the general-type column heat exchanger 410 for preheating a raw material. According to one exemplary embodiment, the general-type column heat exchanger 310 for producing steam may be arranged at a piping system through which the general-type column top stream 220 in the general-type distillation column 200 flows, for example, arranged at a front stage of the general-type column condenser 202, so that the general-type column top stream 220 may pass through the general-type column heat exchanger 310 for producing steam, and then pass through the general-type column condenser 202. Then, some of the general-type column top stream 220 may be refluxed to the general-type distillation column 200. Also, the general-type column heat exchanger 410 for preheating a raw material may be arranged at a piping system through which the divided-type column top stream 120 in the divided-wall distillation column 100, and the raw material 110 flowing into the general-type distillation column 200 flow, for example, arranged at a front stage of the divided-type column condenser 102, so that the divided-type column top stream 120 may pass through the general-type column heat exchanger 410 for preheating a raw material, and then pass through the divided-type column condenser 102. Then, some of the divided-type column top stream 120 may be refluxed to the divided-wall distillation column 100.

The general-type column top stream 220 may pass through the general-type column heat exchanger 310 for producing steam, and exchange heat with external water to produce steam, and the steam produced in the general-type column heat exchanger 310 for producing steam may, for example, be used in a heating process in which the heater is used before the raw material 110 is allowed to flow in the divided-wall distillation column 100. The divided-type column top stream 120 may pass through the general-type column heat exchanger 410 for preheating a raw material, and exchange heat with the raw material 110 flowing into the general-type column raw material feed region 206 so as to preheat the raw material 110. When the preparing device includes the general-type column heat exchanger 310 for producing steam, and the general-type column heat exchanger 410 for preheating a raw material, the steam produced in the general-type column heat exchanger 310 for producing steam may be used in various fields, and an effect of cutting the cost consumed in a condensation process in which the general-type column condenser 202 is used may be achieved by reducing the quantity of cooling water used in the condensation process before the general-type column top stream 220 is refluxed to the general-type column top region 204. At the same time, as the divided-type column top stream 120 exchanges heat with the raw material 110 flowing into the general-type distillation column 200 in the general-type column heat exchanger 410 for preheating a raw material, an effect of cutting the cost consumed in a condensation process in which the divided-type column condenser 102 is used may be further achieved by reducing the quantity of cooling water used in the condensation process before the overhead stream in the divided-wall distillation column 100 is refluxed to the divided-wall distillation column 100. Also, the energy consumed in a heater configured to raise a temperature of the raw material 110 flowing into the general-type distillation column 200, or in the general-type column reboiler 203 configured to heat the general-type column bottom stream 230 discharged from the general-type column bottom region 205 of the general-type distillation column 200 may be reduced. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 12 to 30. Also, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 10 to 50, more preferably 2.5 to 19.5. When the reflux ratio of the divided-type column top stream 120 is adjusted in a range of 100 or less, preferably 20.2 or less, as described above, the energy consumed to reflux the divided-type column top stream, which is refluxed to the divided-wall distillation column 100 in the divided-type column top stream 120 which exchanges heat by means of the general-type column heat exchanger 410 for preheating a raw material and has a temperature of 105 to 120° C., may be minimized, and some of the divided-type column top stream 120 may be simultaneously produced as a high-purity product. Also, when the reflux ratio of the general-type column top stream 220 is adjusted in a range of 100 or less, preferably 8.5 or less, as described above, the energy consumed to reflux the general-type column top stream, which is refluxed to the general-type distillation column 200 in the general-type column top stream 220 which exchanges heat with water by means of the general-type column heat exchanger 310 for producing steam and has a temperature of 100 to 120° C., may be minimized, and some of the general-type column top stream 220 may be simultaneously produced as a high-purity product.

FIG. 13 is a diagram showing an exemplary preparing device according to an eleventh exemplary embodiment of the present application.

According to one exemplary embodiment, the preparing device may include the divided-type column heat exchanger 300 for producing steam, the general-type column heat exchanger 310 for producing steam, and the general-type column heat exchanger 410 for preheating a raw material, as shown in FIG. 13. The divided-type column heat exchanger 300 for producing steam may be arranged at a piping system through which the divided-type column top stream 120 in the divided-wall distillation column 100 flows, for example, arranged at a front stage of the divided-type column condenser 102, so that the divided-wall overhead stream may pass through the divided-type column heat exchanger 300 for producing steam, and then pass through the divided-type column condenser 102. Then, some of the divided-wall overhead stream may be refluxed to the divided-wall distillation column 100. Also, the general-type column heat exchanger 310 for producing steam may be arranged at a piping system through which the general-type column top stream 220 in the general-type distillation column 200 flows, for example, arranged at a front stage of the general-type column condenser 202, so that the general-type column top stream 220 may pass through the general-type column heat exchanger 310 for producing steam, and then pass through the general-type column condenser 202. Then, some of the general-type column top stream 220 may be refluxed to the general-type distillation column 200. Meanwhile, the general-type column heat exchanger 410 for preheating a raw material may be arranged at a piping system through which the product stream 140 in the divided-wall distillation column 100, and the raw material 110 in the general-type distillation column 200 flow.

The general-type column top stream 220 and the divided-type column top stream 120 may pass through the general-type column heat exchanger 310 for producing steam and the divided-type column heat exchanger 300 for producing steam, respectively, and exchange heat with external water to produce steam, and the steam produced in the general-type column heat exchanger 310 for producing steam and the divided-type column heat exchanger 300 for producing steam may, for example, be used in a heating process in which the heater is used before the raw material 110 is allowed to flow in the divided-wall distillation column 100. The product stream 140 in the divided-wall distillation column 100 may pass through the general-type column heat exchanger 410 for preheating a raw material, and exchange heat with the raw material 110 flowing into the general-type column raw material feed region 206 so as to preheat the raw material 110. When the preparing device includes the general-type and divided-type column heat exchanger 300 for producing steam, and the general-type column heat exchanger 410 for preheating a raw material, the steam produced in the general-type and divided-type column heat exchanger 300 for producing steam may be used in various fields, and an effect of cutting the cost consumed in a condensation process in which the general-type column condenser 202 and the divided-type column condenser 102 are used may be achieved by reducing the quantity of cooling water used in the condensation process before the general-type column top stream 220 and the divided-type column top stream 120 are refluxed to the general-type column top region 204 and the divided-type column top region 104, respectively. At the same time, as the product stream 140 in the divided-wall distillation column 100 exchanges heat with the raw material 110 flowing into the general-type distillation column 200 in the general-type column heat exchanger 410 for preheating a raw material, an effect of cutting the cost consumed in a cooling process in which a cooler 108 is used may be further achieved by reducing the quantity of cooling water used in the cooling process before the stream including n-butanol is condensed to be produced as a product. Also, the energy consumed in a heater configured to raise a temperature of the raw material 110 flowing into the general-type distillation column 200, or in the general-type column reboiler 203 configured to heat the general-type column bottom stream 230 discharged from the general-type column bottom region 205 of the general-type distillation column 200 may be reduced. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 13 to 30. Also, the general-type column top stream 220 refluxed to the general-type distillation column 200 after the heat exchange is completed may have a reflux ratio of 1 to 100. In a thermodynamic aspect, the reflux ratio of the general-type column top stream 220 may be preferably in a range of 10 to 50, more preferably 2.3 to 19.2. When the raw material whose heat exchange is completed by means of the general-type column heat exchanger for preheating a raw material flows into the general-type distillation column 200, and then flows out from the general-type column top region 204 at a temperature of 100 to 120° C., the energy consumed to reflux the general-type column top stream, which is refluxed to the general-type distillation column 200 in the general-type column top stream 220 which exchanges heat by means of the general-type column heat exchanger 310 for producing steam and has a temperature of 105 to 120° C., may be minimized, and some of the column top stream may be simultaneously produced as a high-purity product by adjusting the reflux ratio of the general-type distillation column 200 in a range of 100 or less, preferably 8.3 or less, as described above. Also, when the raw material whose heat exchange is completed by means of the general-type column heat exchanger 410 for preheating a raw material flows into the general-type distillation column 200, and some of the general-type column bottom stream 230 flowing out from the general-type column bottom region 205 at a temperature of 115 to 140° C. then flows into the divided-wall distillation column 100, the energy consumed to reflux the divided-type column top stream, which is refluxed to the divided-wall distillation column 100 in the divided-type column top stream 120 which exchanges heat with water by means of the divided-type column heat exchanger 300 for producing steam and has a temperature of 105 to 120° C., may be minimized, and some of the divided-type column top stream 120 may be simultaneously produced as a high-purity product by adjusting the reflux ratio of the divided-wall distillation column 100 in a range of 100 or less, preferably 20 or less, as described above.

Although not shown, the exemplary device for preparing an alkanol according to one exemplary embodiment of the present application may also include at least two general-type column heat exchangers for preheating a raw material. For example, when the preparing device include two general-type column heat exchangers for preheating a raw material, the general-type column top stream may exchange heat with the raw material flowing into the low-temperature general-type distillation column by means of a first general-type column heat exchanger for preheating a raw material so as to preheat the raw material flowing into the general-type distillation column. When the raw material is not sufficiently preheated, the product stream in the divided-wall distillation column, and the raw material flowing into the general-type distillation column may be further preheated by means of a second general-type column heat exchanger for preheating a raw material. According to one exemplary embodiment, the first general-type column heat exchanger for preheating a raw material may be arranged at a piping system through which the general-type column top stream in the general-type distillation column flows, for example, arranged at a front stage of the general-type column condenser, so that the general-type column top stream may pass through the first general-type column heat exchanger for preheating a raw material, and then pass through the general-type column condenser. Then, some of the general-type column top stream may be refluxed to the divided-wall distillation column. Also, the second general-type column heat exchanger for preheating a raw material may be arranged at a piping system through which the product stream in the divided-wall distillation column, and the raw material in the general-type distillation column flow. Therefore, the energy consumed in a heater configured to raise a temperature of the raw material flowing into the general-type distillation column, or in a reboiler configured to heat the column bottom stream discharged from the column bottom region of the general-type distillation column may be reduced. Further, the cost spent in a condensation process in which the general-type column condenser is used may be cut by reducing the quantity of cooling water used in the condensation process before the low boiling point stream in the general-type distillation column is refluxed to the general-type column top region of the general-type distillation column. According to one exemplary embodiment, the temperature of the product stream may be regulated so that a difference in temperature ($\Delta T_{min}$) between the product stream and the raw material preheated by means of the general-type column heat exchanger for preheating a raw material is greater than or equal to 5° C. For example, the difference in temperature ($\Delta T_{min}$) may be regulated by pressurizing or depressurizing the pipe through which the product stream flows. In this case, the general-type column top stream refluxed to the general-type distillation column after the heat exchange is completed may also have a reflux ratio of 1 to 100. In a thermodynamic aspect, the reflux ratio of the general-type column top stream may be preferably in a range of 10 to 50, more preferably 10.5 to 18.5. When the reflux ratio of the general-type column top stream is adjusted in a range of 100 or less, preferably 17 or less, as described above, the energy consumed to reflux the general-type column top stream, which exchanges heat by means of the first divided-type column heat exchanger for preheating a raw material and is then refluxed to the general-type distillation column in the general-type column top stream having a temperature of 95 to 115° C., may be minimized, and some of the general-type column top stream may be simultaneously produced as a high-purity product.

Another aspect of the present application provides a method of preparing an alkanol. For example, the preparing method may be performed using the above-described device for preparing an alkanol. The exemplary preparing method may include introducing a raw material 110 including a compound represented by the following Formula 1 and an isomer thereof into a divided-wall distillation column 100 to separate the compound of Formula 1 and isomer thereof from the raw material 110, introducing a product stream 140 in the divided-wall distillation column 100, which includes the separated compound of Formula 1 and isomer thereof, into a general-type distillation column 200 to separate the isomer of the compound of Formula 1, and allowing some or all of at least one of inflow and outflow streams in the divided-wall distillation column and the general-type distillation column to exchange heat:

R—OH  [Formula 1]

In Formula 1, R represents an alkyl group.

According to one exemplary embodiment of the present application, in the preparing method, some or all of at least one of an column top stream in the divided-wall distillation column, and an column top stream in the general-type distillation column may exchange heat with external water, or some or all of at least one of the column top stream in the divided-wall distillation column, and the column top stream in the general-type distillation column may exchange heat with the raw material introduced into the divided-wall distillation column.

For example, in the preparing method, at least one of an column top stream 120 in the divided-wall distillation column 100, and an column top stream 220 in the general-type distillation column 200 may exchange heat with external water.

At least one of the column top stream 120 in the divided-wall distillation column 100, and the column top stream 220 in the general-type distillation column 200 may exchange heat with water outside the distillation column to produce high-temperature steam. In this case, the divided-type column top stream 120 refluxed to the divided-wall distillation column 100 after the heat exchange is completed may have a reflux ratio of 1 to 100. In a thermodynamic aspect, the reflux ratio of the divided-type column top stream 120 may be preferably in a range of 10 to 60, more preferably 13 to 20. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 10 to 50, more preferably 13 to 25.

In the preparing method, at least one of the column top stream 120 in the divided-wall distillation column 100, and the column top stream 220 in the general-type distillation column 200 may also exchange heat with the raw material 110 introduced into the divided-wall distillation column 100.

At least one of the column top stream 120 in the divided-wall distillation column 100, and the column top stream 220 in the general-type distillation column 200 may exchange heat with the low-temperature raw material 110 flowing into the low-temperature divided-wall distillation column 100 to preheat the raw material 110 flowing into the divided-wall distillation column 100. Therefore, the energy consumed in a heater configured to raise a temperature of the raw material 110 flowing into the divided-wall distillation column 100, or a reboiler configured to heat the column bottom stream discharged from the column bottom region of the divided-wall distillation column 100 may be reduced. Further, the cost spent in a condensation process in which a condenser is used may be cut by reducing the quantity of cooling water used in the condensation process before at least one of the column top stream 120 in the divided-wall distillation column 100, and the column top stream 220 in the general-type distillation column 200 is refluxed to a divided-type column top region 104 and a general-type column top region 204, respectively. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 60, more preferably 10 to 18. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 10 to 50, more preferably 10 to 20.

In the exemplary preparing method, the column top stream 220 in the general-type distillation column 200 may also exchange heat with external water, and the column top stream 120 in the divided-wall distillation column 100 may exchange heat with the raw material 110 introduced into the divided-wall distillation column 100. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 60, more preferably 12 to 20. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 10 to 50, more preferably 13 to 25.

In the preparing method, the column top stream 120 in the divided-wall distillation column 100 may also exchange heat with external water, and the column top stream 220 in the general-type distillation column 200 may exchange heat with the raw material 110 introduced into the divided-wall distillation column 100. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 60, more preferably 11 to 19. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 10 to 50, more preferably 12 to 25.

The preparing method according to one exemplary embodiment of the present application may also include introducing the raw material 110 including a compound represented by the following Formula 1 and an isomer thereof into a general-type distillation column 200 to separate the compound of Formula 1 and isomer thereof from the raw material 110, introducing a column bottom stream in the general-type distillation column 200, which includes the separated compound of Formula 1 and isomer thereof, into a divided-wall distillation column 100 to separate the isomer of the compound of Formula 1, and allowing some or all of at least one of inflow and outflow streams in the divided-wall distillation column and the general-type distillation column to exchange heat:

R—OH [Formula 1]

In Formula 1, R represents an alkyl group.

According to one exemplary embodiment, in the preparing method, some or all of at least one of an column top stream in the divided-wall distillation column, and an column top stream in the general-type distillation column may exchange heat with external water, or some or all of at least one stream selected from the group consisting of an column top stream in the divided-wall distillation column, a product stream, and an column top stream in the general-type distillation column may exchange heat with the raw material introduced into the general-type distillation column.

For example, in the preparing method, at least one of an column top stream 120 in the divided-wall distillation column 100, and an column top stream 220 in the general-type distillation column 200 may exchange heat with external water.

At least one of the column top stream 120 in the divided-wall distillation column 100, and the column top stream 220 in the general-type distillation column 200 may exchange heat with water outside the distillation column to produce high-temperature steam. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 50, more preferably 13.5 to 33.5. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 5 to 40, more preferably 6 to 25.5.

In the preparing method, at least one of the column top stream 120 in the divided-wall distillation column 100, and the column top stream 220 in the general-type distillation column 200 may also exchange heat with the raw material 110 introduced into the general-type distillation column 200.

At least one of the overhead stream 120 in the divided-wall distillation column 100, and the column top stream 220 in the general-type distillation column 200 may exchange heat with the low-temperature raw material 110 flowing into the low-temperature general-type distillation column 200 so as to preheat the raw material 110 flowing into the general-type distillation column 200. Therefore, the energy consumed in a heater configured to raise a temperature of the raw material 110 flowing into the general-type distillation column 200, or in a general-type column reboiler 203 configured to heat a general-type column bottom stream 230 discharged from a general-type column bottom region 205 of the general-type distillation column 200 may be reduced. Further, the cost spent in a condensation process in which the condenser is used may be cut by reducing the quantity of cooling water used in the condensation process before at least one of the column top stream 120 in the divided-wall distillation column 100, and the column top stream 220 in the general-type distillation column 200 is refluxed to the divided-type column top region 104 and the general-type column top region 204, respectively. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 50, more preferably 13 to 33. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 5 to 40, more preferably 3 to 20.

In the exemplary preparing method, the column top stream 120 in the divided-wall distillation column 100 may exchange heat with external water, and the column top stream 220 in the general-type distillation column 200 may exchange heat with the raw material 110 introduced into the general-type distillation column 200. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 60, more preferably 13 to 33. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 10 to 50, more preferably 3 to 20.

In the preparing method, the column top stream 220 in the general-type distillation column 200 may also exchange heat with external water, and the column top stream 120 in the divided-wall distillation column 100 may exchange heat with the raw material 110 introduced in the general-type distillation column 200. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may be preferably adjusted in a range of 10 to 60, more preferably 12 to 30. Also, the reflux ratio of the general-type column top stream 220 refluxed to the general-type distillation column 200 after the heat exchange is completed may be adjusted in a range of 1 to 100. In a thermodynamic aspect, the reflux ratio of the general-type column top stream 220 may be preferably adjusted in a range of 10 to 50, more preferably 2.5 to 19.5.

According to one exemplary embodiment, in the preparing method, the column top streams 120 and 220 in the general-type distillation column 200 and the divided-wall distillation column 100 may also exchange heat with external water, and the product stream 140 in the divided-wall distillation column 100 may exchange heat with the raw material 110 introduced into the general-type distillation column 200. In this case, the reflux ratio of the divided-type column top stream 120 refluxed to the divided-wall distillation column 100 after the heat exchange is completed may be adjusted in a range of 1 to 100. In a thermodynamic aspect, the reflux ratio of the divided-type column top stream 120 may preferably adjusted in a range of 10 to 60, more preferably 13 to 30. Also, the reflux ratio of the general-type column top stream 220 refluxed to the general-type distillation column 200 after the heat exchange is completed may adjusted in a range of 1 to 100. In a thermodynamic aspect, the reflux ratio of the general-type column top stream 220 may be preferably adjusted in a range of 10 to 50, more preferably 2.3 to 19.2.

Advantageous Effects

According to one exemplary embodiment of the present application, energy saving can be promoted upon the preparation of an alkanol by reducing the quantity of steam used in a reboiler of the device or the quantity of cooling water used in a condenser, and the steam generated from a heat exchanger for producing steam can be used in a variety of fields. Also, a high-purity alkanol can be prepared according to one exemplary embodiment of the present application.

Best Mode

Hereinafter, the present application will be described in further detail with reference to Examples according to the present application and Comparative Example not according to the present application, but the scope of the present application is not limited to the following Examples.

EXAMPLE 1

N-butanol was prepared using a device in which a divided-wall distillation column and a general-type distillation column were sequentially connected as shown in FIG. 1. Specifically, a raw material including iso-butanol and n-butanol was introduced into the divided-wall distillation column to perform a separation process. Here, the conditions of the separation process were set so that the operating pressure and operating temperature of a lower portion of the divided-wall distillation column were approximately 2.5 Kg/cm$^2$ and approximately 140° C., respectively, and the operating pressure and operating temperature of an upper portion of the divided-wall distillation column were approximately 1.5 Kg/cm$^2$ and approximately 103° C., respectively. Also, some of a divided-type column bottom stream having a high boiling point discharged from a divided-type column bottom region of the divided-wall distillation column was again introduced into the divided-wall distillation column through a divided-type column reboiler. In addition, some of a divided-type column top stream including a low boiling point stream, and water discharged from a divided-type column top region of the divided-wall distillation column, were re-introduced into the divided-wall distillation column through a divided-type column condenser, and the rest of the divided-type column top stream were separated as products. Also, a stream including iso-butanol and n-butanol, which was a product stream in the divided-wall distillation column, was introduced into the general-type distillation column to perform a separation process. Here, the conditions of the separation process were set so that the operating pressure and operating temperature of a lower portion of the general-type distillation column were approximately 1.8 $Kg/cm^2$ and approximately 135° C., respectively, and the operating pressure and operating temperature of an upper portion of the general-type distillation column were approximately 1.0 $Kg/cm^2$ and approximately 105° C., respectively. Also, some of n-butanol discharged from a general-type column bottom region of the general-type distillation column was again introduced into the general-type distillation column through a general-type column reboiler, and the rest of the n-butanol was separated as a product. Also, some of iso-butanol discharged from a general-type column top region of the general-type distillation column was re-introduced into the general-type distillation column through a general-type column condenser, and the rest of the iso-butanol was separated as a product. In this case, the reflux ratios of the divided-type column top stream in the divided-wall distillation column, and the general-type column top stream refluxed to the general-type distillation column were set so that the divided-type column top stream and the general-type column top stream had reflux ratios of 13 to 20 and 14 to 26, respectively.

EXAMPLE 2

N-butanol and iso-butanol were separated in the same manner as in Example 1, except that iso-butanol discharged from the general-type column top region of the general-type distillation column passed through a general-type column heat exchanger for producing steam before the iso-butanol flowed through the general-type column condenser, as shown in FIG. 4. In this case, the reflux ratios of the divided-type column top stream in the divided-wall distillation column, and the general-type column top stream refluxed to the general-type distillation column were set so that the divided-type column top stream and the general-type column top stream had reflux ratios of 13 to 20 and 13 to 25, respectively.

EXAMPLE 3

N-butanol and iso-butanol were separated in the same manner as in Example 1, except that iso-butanol discharged from the general-type column top region of the general-type distillation column passed through the general-type column heat exchanger for producing steam before the iso-butanol flowed through the general-type column condenser, and a low boiling point component and water discharged from the divided-type column top region of the divided-wall distillation column passed through a divided-type column heat exchanger for producing steam before the low boiling point component and water passed through the divided-type column condenser, as shown in FIG. 5. In this case, the reflux ratios of the divided-type column top stream in the divided-wall distillation column, and the general-type column top stream refluxed to the general-type distillation column were set so that the divided-type column top stream and the general-type column top stream had reflux ratios of 15 to 23 and 13 to 25, respectively.

EXAMPLE 4

N-butanol and iso-butanol were separated in the same manner as in Example 1, except that iso-butanol discharged from the general-type column top region of the general-type distillation column exchanged heat with a raw material, which had been introduced into the divided-wall distillation column, by means of a divided-type column heat exchanger for preheating a raw material before the iso-butanol flowed through the general-type column condenser, as shown in FIG. 6. In this case, the reflux ratios of the divided-type column top stream in the divided-wall distillation column, and the general-type column top stream refluxed to the general-type distillation column were set so that the divided-type column top stream and the general-type column top stream had reflux ratios of 10 to 18 and 10 to 20, respectively.

EXAMPLE 5

N-butanol and iso-butanol were separated in the same manner as in Example 1, except that a low boiling point component and water discharged from the divided-type column top region of the divided-wall distillation column exchanged heat with a raw material, which had been introduced into the divided-wall distillation column, by means of the divided-type column heat exchanger for preheating a raw material before the low boiling point component and water flowed through the divided-type column condenser, and iso-butanol discharged from the general-type column top region of the general-type distillation column passed through the general-type column heat exchanger for producing steam before the iso-butanol flowed through the general-type column condenser, as shown in FIG. 7. In this case, the reflux ratios of the divided-type column top stream in the divided-wall distillation column, and the general-type column top stream refluxed to the general-type distillation column were set so that the divided-type column top stream and the general-type column top stream had reflux ratios of 12 to 20 and 13 to 25, respectively.

EXAMPLE 6

N-butanol and iso-butanol were separated in the same manner as in Example 1, except that iso-butanol discharged from the general-type column top region of the general-type distillation column exchanged heat with a raw material, which had been introduced into the divided-wall distillation column, by means of the divided-type column heat exchanger for preheating a raw material before the iso-butanol flowed through the general-type column condenser, and a low boiling point component and water discharged from the divided-type column top region of the divided-wall distillation column passed through the divided-type column heat exchanger for producing steam before the low boiling point component and water flowed through the divided-type column condenser, as shown in FIG. 8. In this case, the reflux ratios of the divided-type column top stream in the divided-wall distillation column, and the general-type column top stream refluxed to the general-type distillation column were set so that the divided-type column top stream and the general-type column top stream had reflux ratios of 11 to 19 and 12 to 25, respectively.

EXAMPLE 7

N-butanol was prepared using a device in which a general-type distillation column and a divided-wall distillation column were sequentially connected as shown in FIG. 9. Specifically, a raw material including iso-butanol and n-butanol was introduced into the general-type distillation column to perform a separation process. Here, the conditions of the separation process were set so that the operating pressure and operating temperature of a lower portion of the general-type distillation column were approximately 1.9 Kg/cm$^2$ and approximately 140° C., respectively, and the operating pressure and operating temperature of an upper portion of the general-type distillation column were approximately 1.5 Kg/cm$^2$ and approximately 100° C., respectively. Also, some of a general-type column bottom stream 230 having a high boiling point discharged from a general-type column bottom region of the general-type distillation column was again introduced into the general-type distillation column through a general-type column reboiler 203, and the rest of the general-type column bottom stream 230 was introduced into the divided-wall distillation column. Also, some of a general-type column top stream including a low boiling point stream and water discharged from a general-type column top region of the general-type distillation column, was re-introduced into the general-type distillation column through a general-type column condenser, and the rest of the general-type column top stream were separated as products. Also, some of a product in a lower portion of the general-type distillation column, that is, a general-type column bottom stream, which included iso-butanol and n-butanol and had a high boiling point, was introduced into the divided-wall distillation column to perform a separation process. Here, the conditions of the separation process were set so that the operating pressure and operating temperature of a lower portion of the divided-wall distillation column were approximately 1.5 Kg/cm$^2$ and approximately 130° C., respectively, and the operating pressure and operating temperature of an upper portion of the divided-wall distillation column were approximately 1.1 Kg/cm$^2$ and approximately 110° C., respectively. Also, some of a divided-type column bottom stream which was a high boiling point component discharged from a divided-type column bottom region of the divided-wall distillation column was again introduced into the divided-wall distillation column through a divided-type column reboiler, and the rest of the divided-type column bottom stream was separated as a product. Also, some of iso-butanol discharged from a divided-type column top region of the divided-wall distillation column was re-introduced into the divided-wall distillation column through a divided-type column condenser, and the rest of the iso-butanol was separated as a product. Further, n-butanol discharged from a product outflow region of the divided-wall distillation column passed through a condenser, and was separated a product. In this case, the reflux ratios of the divided-type column top stream in the divided-wall distillation column, and the general-type column top stream refluxed to the general-type distillation column were set so that the divided-type column top stream and the general-type column top stream had reflux ratios of 13 to 33 and 6 to 25, respectively.

EXAMPLE 8

N-butanol and iso-butanol were separated in the same manner as in Example 7, except that a low boiling point component and water discharged from the general-type column top region of the general-type distillation column passed through a general-type column heat exchanger for producing steam before the low boiling point component and water flowed through the general-type column condenser, and iso-butanol discharged from the divided-type column top region of the divided-wall distillation column passed through a divided-type column heat exchanger for producing steam before the iso-butanol flowed through the divided-type column condenser, as shown in FIG. 10. In this case, the reflux ratios of the divided-type column top stream in the divided-wall distillation column, and the general-type column top stream refluxed to the general-type distillation column were set so that the divided-type column top stream and the general-type column top stream had reflux ratios of 13.5 to 33.5 and 6.5 to 25.5, respectively.

EXAMPLE 9

N-butanol and iso-butanol were separated in the same manner as in Example 7, except that the low boiling point component and water discharged from the general-type column top region of the general-type distillation column exchanged heat with a raw material, which had been introduced into the general-type distillation column, by means of a general-type column heat exchanger for preheating a raw material before the low boiling point component and water flowed through the general-type column condenser, and iso-butanol discharged from the divided-type column top region of the divided-wall distillation column passed through the divided-type column heat exchanger for producing steam before the iso-butanol flowed through the divided-type column condenser, as shown in FIG. 11. In this case, the reflux ratios of the divided-type column top stream in the divided-wall distillation column, and the general-type column top stream refluxed to the general-type distillation column were set so that the divided-type column top stream and the general-type column top stream had reflux ratios of 13 to 33 and 3 to 20, respectively.

EXAMPLE 10

N-butanol and iso-butanol were separated in the same manner as in Example 7, except that iso-butanol discharged from the divided-type column top region of the divided-wall distillation column exchanged heat with a raw material, which had been introduced into the general-type distillation column, by means of the general-type column heat exchanger for preheating a raw material before the iso-butanol flowed through the divided-type column condenser, and the low boiling point component and water discharged from the general-type column top region of the general-type distillation column passed through the general-type column heat exchanger for producing steam before the low boiling point component and water flowed through the general-type column condenser, as shown in FIG. 12. In this case, the reflux ratios of the divided-type column top stream in the divided-wall distillation column, and the general-type column top stream refluxed to the general-type distillation column were set so that the divided-type column top stream and the general-type column top stream had reflux ratios of 12 to 30 and 2.5 to 19.5, respectively.

EXAMPLE 11

N-butanol and iso-butanol were separated in the same manner as in Example 7, except that n-butanol discharged from the product outflow region of the divided-wall distillation column exchanged heat with a raw material, which had been introduced into the general-type distillation column, by means of the general-type column heat exchanger for preheating a raw material before the n-butanol flowed through the condenser, the low boiling point component and water discharged from the general-type column top region of the general-type distillation column passed through the general-type column heat exchanger for producing steam before the low boiling point component and water flowed through the general-type column condenser, and iso-butanol discharged from the divided-type column top region of the divided-wall distillation column passed through the divided-type column heat exchanger for producing steam before the iso-butanol flowed through the divided-type column condenser, as shown in FIG. 13. In this case, the reflux ratios of the divided-type column top stream in the divided-wall distillation column, and the general-type column top stream refluxed to the general-type distillation column were set so that the divided-type column top stream and the general-type column top stream had reflux ratios of 13 to 30 and 2.3 to 19.2, respectively.

COMPARATIVE EXAMPLE 1

A device for preparing an alkanol in which three general-type distillation columns were sequentially connected was configured so that a raw material including n-butanol and iso-butanol was introduced into the device, as shown in FIG. 14. In the device as shown in FIG. 14, a low boiling point component and water with a temperature of 100° C., which were discharged from an upper portion of a first general-type distillation column, were condensed at 50° C. using a condenser. Thereafter, some of the low boiling point component was refluxed to an column top region of the general-type distillation column, and the rest of the low boiling point component was separated as a product. Also, a high boiling point component with a temperature of 140° C., which was discharged from a lower portion of the first general-type distillation column and included n-butanol and iso-butanol, was heated at 141° C. using a reboiler. Thereafter, some of the high boiling point component was refluxed again to a column bottom region of the general-type distillation column, and the rest of the high boiling point component was introduced into a second general-type distillation column. A stream, which was discharged from an upper portion of the second general-type distillation column, included iso-butanol and had a temperature of 120° C., was condensed at 50° C. using a condenser. Thereafter, some of the stream was refluxed again to the column top region of the general-type distillation column, and the rest of the stream was separated as a product. Also, a high boiling point component, which was discharged from a lower portion of the second general-type distillation column, included n-butanol and had a temperature of 142° C., was heated at 143° C. using a reboiler. Thereafter, some of the high boiling point component was refluxed again to the column bottom region of the general-type distillation column, and the rest of the high boiling point component was introduced into a third general-type distillation column. Next, a stream, which was discharged from an upper portion of the third general-type distillation column, included n-butanol and had a temperature of 130° C., was condensed at 50° C. using a condenser. Thereafter, some of the stream was refluxed again to the column top region of the general-type distillation column, and the rest of the stream was separated as a product. Also, a high boiling point component, which was discharged from a lower portion of the third general-type distillation column and had a temperature of 145° C. was heated at 146° C. using a reboiler. Thereafter, some of the high boiling point component was refluxed again to the column bottom region of the general-type distillation column, and the rest of the high boiling point component was introduced into the third general-type distillation column. In this case, the reflux ratio of the general-type column top stream refluxed to the general-type distillation column was set so that the general-type column top stream had a reflux ratio of 0.5 to 50.

Measurement of Energy Used

When n-butanol and iso-butanol were separated using each of the preparing devices used in Examples 1 to 11 and Comparative Example 1, the consumption of energy was measured. The results are listed in the following Table 1.

TABLE 1

| | Consumption of energy used in each column (gal/hr) | | Total consumption of energy (gal/hr) | Reduction in energy (%) |
|---|---|---|---|---|
| Example 1 | DWC | 4.24 | 13.24 | 20.5 |
| | General-type distillation column | 9.00 | | |
| Example 2 | DWC | 4.24 | 12.69 | 23.8 |
| | General-type distillation column | 8.45 | | |
| Example 3 | DWC | 3.69 | 12.14 | 27.1 |
| | General-type distillation column | 8.45 | | |
| Example 4 | DWC | 3.49 | 12.49 | 25.0 |
| | General-type distillation column | 9.00 | | |
| Example 5 | DWC | 3.45 | 11.90 | 28.5 |
| | General-type distillation column | 8.00 | | |
| Example 6 | DWC | 2.90 | 11.90 | 28.5 |
| | General-type distillation column | 9.00 | | |
| Example 7 | General-type distillation column | 2.74 | 10.74 | 35.5 |
| | DWC | 8.00 | | |
| Example 8 | General-type distillation column | 2.19 | 9.64 | 42.1 |
| | DWC | 7.45 | | |
| Example 9 | General-type distillation column | 1.95 | 9.40 | 43.5 |
| | DWC | 7.45 | | |
| Example 10 | General-type distillation column | 1.41 | 9.41 | 43.5 |
| | DWC | 8.00 | | |
| Example 11 | General-type distillation column | 1.41 | 8.86 | 46.8 |
| | DWC | 7.45 | | |
| Comparative Example 1 | General-type distillation column | 2.74 | 16.65 | — |
| | General-type distillation column | 9.80 | | |
| | General-type distillation column | 4.11 | | |

As listed in Table 1, it was revealed that the preparing devices used in Examples 1 to 11 of the present application had an energy-saving effect up to 46.8% when the n-butanol and iso-butanol were separated using the preparing devices, compared to the preparing device of Comparative Example 1. Also, it was revealed that the preparing device in which the raw material was introduced into the divided-wall distillation column through the general-type distillation column had a superior energy-saving effect to the preparing device in which the raw material was introduced into the general-type distillation column through the divided-wall distillation column. This is because the energy efficiency of the divided-wall distillation column is superior to the general-type distillation column. That is, since n-butanol and iso-butanol have a similar boiling point, a product having desired specifications may be produced with less consumption of energy when n-butanol and iso-butanol are separated using the divided-wall distillation column, compared to when n-butanol and iso-butanol are separated using the conventional distillation columns. Therefore, when a four-or-more-component material including the components having a similar boiling point is separated into the respective components, it may be desirable to first separate the low boiling point component through the general-type distillation column, and then separate the respective components having a similar boiling point at the divided-wall distillation column in terms of energy efficiency.

The invention claimed is:

1. A device for preparing n-butanol comprising:
a divided-wall distillation column, a divided-type column reboiler, and a divided-type column condenser, both of which are fluidically connected to the divided-wall distillation column;
a general-type distillation column, a general-type column reboiler, and a general-type column condenser, both of which are fluidically connected to the general-type distillation column; and
a heat exchanger arranged at a stage(s) prior to the divided-type column condenser and/or the general-type column condenser and configured such that some or all of at least one of an inflow stream and at least one of an outflow stream in the divided-wall distillation column and the general-type distillation column exchanges heat,
wherein the divided-wall distillation column is divided into a divided-type column raw material feed region, a product outflow region, a divided-type column top region, and a divided-type column bottom region, and the general-type distillation column is divided into a general-type column raw material feed region, a general-type column top region, and a general-type column bottom region,
a raw material comprising n-butanol and isobutanol flows into the divided-type column raw material feed region, and the raw material flowing into the divided-type column raw material feed region is separated into a product stream, a divided-type column top stream, and a divided-type column bottom stream to flow out therefrom,
the divided-type column top stream flows out from the divided-type column top region and passes through the divided-type column condenser, some of the divided-type column top stream passing through the divided-type column condenser is refluxed to the divided-wall distillation column, the divided-type column bottom stream flows out from the divided-type column bottom region, and some of the divided-type column bottom stream is refluxed to the divided-wall distillation column through the divided-type column reboiler,
the product stream flows out from the product outflow region and flows into the general-type column raw material feed region, the product stream flowing into the general-type column raw material feed region is separated into a general-type column top stream and a general-type column bottom stream to flow out therefrom, and
the general-type column bottom stream flows out from the general-type column bottom region, some of the general-type column bottom stream is refluxed to the general-type distillation column through the general-type column reboiler and the rest of the general-type column bottom stream is separated as a product comprising n-butanol, the general-type column top stream flows out from the general-type column top region and passes through the general-type column condenser, and some of the general-type column top stream passing through the general-type column condenser is refluxed to the general-type distillation column to separate n-butanol and isobutanol and the rest of the general-type column top stream is separated as a product comprising isobutanol,
wherein the divided-type column top stream refluxed to the divided-wall distillation column after the heat exchange incomplete has a reflux ratio of 10 to 23,
wherein the general-type column top stream refluxed to the general-type distillation column after the heat exchange is complete has a reflux ratio of 10 to 26, and
wherein n-butanol is prepared.

2. The device of claim 1, wherein, in the heat exchanger, some or all of at least one of the divided-type column top stream and the general-type column top stream exchanges heat with external water at the stage(s) prior to the divided-type column condenser and/or the general-type column condenser, or some or all of at least one of the divided-type column top stream and the general-type column top stream exchanges heat with the raw material flowing into the divided-type column raw material feed region at the stage(s) prior to the divided-type column condenser and/or the general-type column condenser so as to raise a temperature of the raw material.

3. The device of claim 1, wherein the heat exchanger is a heat exchanger for producing steam in which at least one of the divided-type column top stream and the general-type column top stream exchanges heat with external water at the stage(s) prior to the divided-type column condenser and/or the general-type column condenser.

4. The device of claim 1, wherein the heat exchanger is a heat exchanger for preheating a raw material in which at least one of the divided-type column top stream and the general-type column top stream exchanges heat with the raw material flowing into the divided-type column raw material feed region at the stage(s) prior to the divided-type column condenser and/or the general-type column condenser so as to raise a temperature of the raw material.

5. The device of claim 1, wherein the device comprises a general-type column heat exchanger for producing steam in which the general-type column top stream exchanges heat with external water at the stage(s) prior to the general-type column condenser, and a divided-type column heat exchanger for preheating a raw material in which the divided-type column top stream exchanges heat with the raw material flowing into the divided-type column raw material feed region at the front stage of the divided-type column condenser so as to raise a temperature of the raw material.

6. The device of claim 1, wherein the device comprises a divided-type column heat exchanger for producing steam in which the divided-type column top stream exchanges heat with external water at the stage(s) prior to the divided-type column condenser, and a divided-type column heat exchanger for preheating a raw material in which the general-type column top stream exchanges heat with the raw material flowing into the divided-type column raw material feed region at the stage(s) prior to the general-type column condenser so as to raise a temperature of the raw material.

7. A device for preparing n-butanol comprising:
a divided-wall distillation column, a divided-type column reboiler, and divided-type column condenser, both of which are fluidically connected to the divided-wall distillation column;
a general-type distillation column, a general-type column reboiler, and a general-type column condenser, both of which are fluidically connected to the general-type distillation column; and
a heat exchanger arranged at a stage(s) prior to the divided-type column condenser and/or the general-type column condenser and configured such that some or all of at least one of inflow and outflow streams in the divided-wall distillation column and the general-type distillation column exchanges heat,
wherein the divided-wall distillation column is divided into a divided-type column raw material feed region, a product outflow region, a divided-type column top region, and a divided-type column bottom region, and the general-type distillation column is divided into a general-type column raw material feed region, a general-type column top region, and a general-type column bottom region,
a raw material comprising n-butanol and isobutanol flows into the general-type column raw material feed region, and the raw material flowing into the general-type column raw material feed region is separated into a general-type column top stream and a general-type column bottom stream to flow out therefrom, the general-type column top stream flows out from the general-type column top region and passes through the general-type column condenser, and some of the general-type column top stream passing through the general-type column condenser is refluxed to the general-type distillation column,
the general-type column bottom stream flows out from the general-type column bottom region, some of the general-type column bottom stream is refluxed to the general-type distillation column through the general-type column reboiler, the rest of the general-type column bottom stream flows into the divided-type column raw material feed region, and the general-type column bottom stream flowing into the divided-type column raw material feed region is separated into a product stream, a divided-type column top stream, and a divided-type column bottom stream to flow out therefrom, and
the divided-type column bottom stream flows out from the divided-type column bottom region, some of the divided-type column bottom stream is refluxed to the divided-wall distillation column through the divided-type column reboiler, the divided-type column top stream flows out from the divided-type column top region and passes through the divided-type column condenser, some of the divided-type column top stream passing through the divided-type column condenser is refluxed to the divided-wall distillation column and the rest is separated as a product comprising iso-butanol, and the product stream flows out from the product outflow region and comprises n-butanol,
wherein the divided-type column top stream refluxed to the divided-wall distillation column after the heat exchange is complete has a reflux ratio of 12 to 33.5,
wherein the general-type column top stream refluxed to the general-type distillation column after the heat exchange is complete has a reflux ratio of 2.3 to 25.5, and
wherein n-butanol is prepared.

8. The device of claim 7, wherein, in the heat exchanger, some or all of at least one of the divided-type column top stream and the general-type column top stream exchanges heat with external water at the stage(s) prior to the divided-type column condenser and/or the general-type column condenser, or some or all of at least one of the divided-type column top stream and the general-type column top stream exchanges heat with the raw material flowing into the general-type column raw material feed region at the stage(s) prior to the divided-type column condenser and/or the general-type column condenser so as to raise a temperature of the raw material.

9. The device of claim 7, wherein the heat exchanger is a heat exchanger for producing steam in which at least one of the divided-type column top stream and the general-type column top stream exchanges heat with external water at the stage(s) prior to the divided-type column condenser and/or the general-type column condenser.

10. The device of claim 7, wherein the heat exchanger is a heat exchanger for preheating a raw material in which at least one of the divided-type column top stream and the general-type column top stream exchanges heat with the raw material flowing into the general-type column raw material feed region at the stage(s) prior to the divided-type column condenser and/or the general-type column condenser so as to raise a temperature of the raw material.

11. The device of claim 7, wherein the device comprises a general-type column heat exchanger for producing steam in which the general-type column top stream exchanges heat with external water at the stage(s) prior to the general-type column condenser, and a general-type column heat exchanger for preheating a raw material in which the divided-type column top stream exchanges heat with the raw material flowing into the general-type column raw material feed region at the stage(s) prior to the divided-type column condenser so as to raise a temperature of the raw material.

12. The device of claim 7, wherein the device comprises a divided-type column heat exchanger for producing steam in which the divided-type column top stream exchanges heat with external water at the stage(s) prior to the divided-type column condenser, and a general-type column heat exchanger for preheating a raw material in which the general-type column top stream exchanges heat with the raw material flowing into the general-type column raw material feed region at the stage(s) prior to the general-type column condenser so as to raise a temperature of the raw material.

13. The device of claim 7, wherein the device comprises a divided-type column heat exchanger for producing steam in which the divided-type column top stream exchanges heat with external water at the stage(s) prior to the divided-type column condenser; a general-type column heat exchanger for producing steam in which the general-type column top stream exchanges heat with external water at the stage(s) prior to the general-type column condenser; and a general-type column heat exchanger for preheating a raw material in which the product stream exchanges heat with the raw material flowing into the general-type column raw material feed region so as to raise a temperature of the raw material.

14. A method of preparing n-butanol, comprising:
providing the device of claim 1;
introducing the raw material comprising n-butanol and iso-butanol into the divided-wall distillation column to separate the n-butanol and iso-butanol from the raw material;
introducing the product stream from the divided-wall distillation column, which comprises the separated n-butanol and iso-butanol, into the general-type distillation column to separate the iso-butanol; and
allowing some or all of at least one of the inflow and at least one of the outflow streams in the divided-wall distillation column and the general-type distillation column to exchange heat
and
wherein some of the divided-type column top stream is refluxed to the divided-wall distillation column after the heat exchange is complete, and has a reflux ratio of 10 to 23,
wherein some of the general-type column top stream is refluxed to the general-type distillation column after the heat exchange is complete, and has a reflux ratio of 10 to 26, and
wherein n-butanol is prepared.

15. The method of claim 14, wherein some or all of at least one of the column top stream from the divided-wall distillation column, and the column top stream from the general-type distillation column exchanges heat with external water, or some or all of at least one of the column top stream from the divided-wall distillation column, and the column top stream from the general-type distillation column exchanges heat with the raw material introduced into the divided-wall distillation column.

16. The method of claim 14, wherein the method comprises: allowing the column top stream from the general-type distillation column to exchange heat with external water, and allowing the column top stream from the divided-wall distillation column to exchange heat with the raw material introduced into the divided-wall distillation column.

17. The method of claim 14, wherein the method comprises: allowing the column top stream from the divided-wall distillation column to exchange heat with external water, and allowing the column top stream from the general-type distillation column to exchange heat with the raw material introduced into the divided-wall distillation column.

18. A method of preparing n-butanol, comprising:
providing the device of claim 7;
introducing the raw material comprising n-butanol and iso-butanol into the general-type distillation column to separate the n-butanol and iso-butanol from the raw material;
introducing the column bottom stream from the general-type distillation column, which comprises the separated n-butanol and iso-butanol, into a divided-wall distillation column to separate the iso-butanol; and
allowing some or all of at least one of the inflow and at least one of the outflow streams in the divided-wall distillation column and the general-type distillation column to exchange heat,
wherein some of the divided-type column top stream is refluxed to the divided-wall distillation column after the heat exchange is complete, and has a reflux ratio of 12 to 33.5,
wherein some of the general-type column top stream is refluxed to the general-type distillation column after the heat exchange is complete, and has a reflux ratio of 2.3 to 25.5, and
wherein n-butanol is prepared.

19. The method of claim 18, wherein some or all of at least one of the column top stream from the divided-wall distillation column, and the column top stream from the general-type distillation column exchanges heat with external water, or some or all of at least one stream selected from the group consisting of the column top stream and the product stream from the divided-wall distillation column, and the column top stream from the general-type distillation column exchanges heat with the raw material introduced into the general-type distillation column.

20. The method of claim 18, wherein the method comprises:
allowing the column top stream from the general-type distillation column to exchange heat with external water, and allowing the column top stream from the divided-wall distillation column to exchange heat with the raw material introduced into the general-type distillation column.

21. The method of claim 18, wherein the method comprises:
allowing the column top stream from the divided-wall distillation column to exchange heat with external water, and allowing the column top stream from the general-type distillation column to exchange heat with the raw material introduced into the general-type distillation column.

22. The method of claim 18, wherein the method comprises:
allowing the column top streams from the general-type distillation column and the divided-wall distillation column to exchange heat with external water, and allowing the product stream from the divided-wall distillation column to exchange heat with the raw material introduced into the general-type distillation column.

* * * * *